United States Patent
Rauscher, III et al.

(10) Patent No.: US 6,307,035 B1
(45) Date of Patent: Oct. 23, 2001

(54) BRCA1 ASSOCIATED POLYNUCLEOTIDE (BAP-1) AND USES THEREFOR

(75) Inventors: Frank J. Rauscher, III, Wayne; David E. Jensen, Philadelphia, both of PA (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 0 days.

(21) Appl. No.: 09/230,196

(22) PCT Filed: Jul. 30, 1997

(86) PCT No.: PCT/US97/13684

§ 371 Date: Jan. 20, 1999

§ 102(e) Date: Jan. 20, 1999

(87) PCT Pub. No.: WO98/05968

PCT Pub. Date: Feb. 12, 1998

Related U.S. Application Data

(60) Provisional application No. 60/038,109, filed on Feb. 19, 1997, now abandoned, and provisional application No. 60/022,997, filed on Aug. 2, 1996, now abandoned.

(51) Int. Cl.$^7$ .......................... C07H 21/02; C12N 15/00; C12N 1/20; C12P 21/06
(52) U.S. Cl. .................. 536/23.1; 435/320.1; 435/252.3; 435/69.1
(58) Field of Search ........................ 536/23.1; 435/320.1, 435/252.3, 69.1

(56) References Cited

U.S. PATENT DOCUMENTS

| | | | |
|---|---|---|---|
| 4,889,806 | * | 12/1989 | Olson et al. . |
| 5,610,031 | * | 3/1997 | Burgeson et al. . |
| 5,912,143 | * | 6/1999 | Bandman et al. . |

FOREIGN PATENT DOCUMENTS

| | | |
|---|---|---|
| 0 699 754 A1 | 3/1996 | (EP) . |
| WO 98/01460 | 1/1998 | (WO) . |
| WO 9812327 | 3/1998 | (WO) . |

OTHER PUBLICATIONS

Database EMEST34, E.B.I. Databases Accession No. T08929; M. Adams et al., "Homosapiens cDNA Clone 5' End Similar to Ubiquitin Carboxyl–Terminal Hydrolase Isozyme L1", (Aug. 6, 1993) XP002134755 (abstract).

D. Jensen et al., "BAP–1, A Novel Protein which Binds to the RING Finger of the BRCA1 Gene Product and Exhibits Properties of a Tumor Suppressor", Proc. Am. Assoc. Cancer Res. Annual Meeting, 38:253 (Mar. 1997) XP000891704.

E. V. Koonin, "Functional Motifs", *Nature Genetics*, New York: NY; 13(3): 266–267 (Jul. 1, 1996) XP002054691, ISSN: 1061–4036.

A.J. Saurin et al., "Does This Have a Familiar RING?", *TIBS Trends in Biochemical Sciences*, EN, Elsevier Publication: Cambridge; 21(6):208–214 (Jun. 1, 1996) XP004050893, ISSN: 0968–0004.

Weber et al., Familial Breast Cancer—Approaching the Isolation of a Susceptibility Gene, Cancer, vol. 74, No. 3, pp. 1013–1020, (Aug. 1, 1994).

Ford et al., The Genetics of Breast and Ovarian Cancer, British Journal of Cancer, vol. 72, pp. 805–812, (1995).

Nomura et al., 'Prediction of the coding sequences of unidentified human genes', Database DDBJ/EMBL/Genbank, Accession No. D87462, (Direct Submission Aug. 27, 1996).

Hillier et al., 'The Washu–Merck EST Project', Database EST–STS, Accession No. N77549, (Direct Submission Apr. 2, 1996).

Hillier et al., 'The WashU–Merck EST Project', Database EST–STS–Three, Accession No. W35227, (Direct Submission May 16, 1996).

Taber's Cyclopedic Medical Dictionary, 16th Ed., F.A. Davis, Philadelphia, p. 1897, 1985.*

Freshney (Culture of Animal Cells, a Manual of Basic Techniques, Alan R. Russ, Inc.,NY, p. 4), 1983.*

Dermer (Bio/Technology, 12:320), 1985.*

Easton et al., "Genetic Linkage Analysis in Familial Breast and Ovarian Cancer: Results from 214 Families", *Am. J. Hu. Genetics*, 52:678–701 (1993).

Friedman et al., "Confirmation of BRCA1 by analysis of germline mutations linked to breast and ovarian cancer in ten familirs", *Nature Genetics*, 8:399–404 (Dec., 1994).

Muto et al., "Frequency of the BRCA1 185delAG Mutation among Jewish Women with Ovarian Cancer and Matched Population Controls", *Cancer Research*, 56:1250–1252 (Mar., 1996).

Couch et al., "Mutations and Polymorphisms in the Familial Early–Onset Breast Cancer (BRCA1) Gene", *Human Mutation*, 8:8–18 (1996).

Reiger et al (Glossary of Genetics and Cytogenetics, Classical and Molecular, 4th Ed., Springer–Verlag, Berlin, p. 18), 1976.*

Orkin et al (Report and Recommendations of the Panel to Assess the NIH investment in Research on Gene Therapy), 1995.*

Marshall (Science, 269:1050–1055), 1995.*

Culver et al (TIG, 10:174–178), 1994.*

(List continued on next page.)

Primary Examiner—Susan Ungar
(74) Attorney, Agent, or Firm—Howson and Howson

(57) ABSTRACT

Nucleic acid and amino acid sequences of a BRCA1 associated protein, BAP-1, are provided. These sequences, the protein, and anti-BAP-1 antibodies are useful in therapeutics and diagnostics for cancers associated with loss of the 3p21 chromosomal region and/or inappropriate BAP-1 levels.

11 Claims, 11 Drawing Sheets

OTHER PUBLICATIONS

Figure 1B:
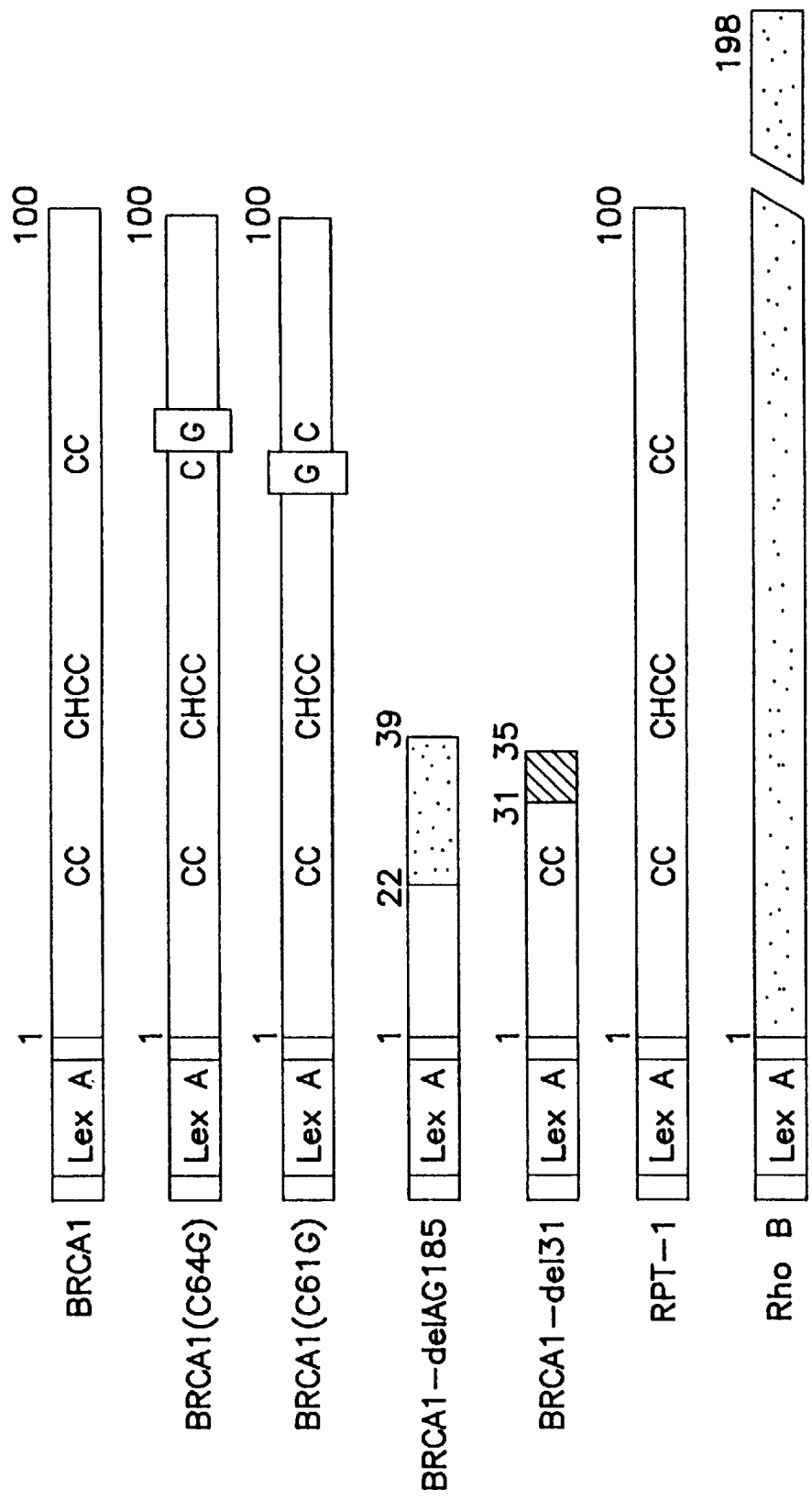

Nature Biotechnology, (15:815), 1997.*
Taber's Cyclopedic Medical Dictionary (16th Ed., F.A. Davis, Philadelphia, p. 492), 1989.*
Freshney (Culture of Animal Cells, A Manual of Basic Technique, Alan R. Liss, Inc., New York, p. 4), 1983.*
Dermer (Bio/Technology, 12:320), 1994.*
Burgess et al (J. Cell Biol., 111:2129–2138), 1990.*
Lazar et al (Molecular and Cellular Biology, 8:1247–1252), 1988.*
Nagase et al (DNA Res., 3:321–329), 1996.*
Hillier et al (Genbank Sequence Database (Accession R56210) National Center for Biotechnology Information, National Library of Medicine, Bethesda, Maryland), 1995.*
Sambrook et al (Molecular Cloning, a Laboratory Manuarl, Cold Spring Harbor Press, p. 16.3–4), 1989.*
Y. Miki et al., "A Strong Candidate for the Breast and Ovarian Cancer Susceptibility Gene BRCA1", *Science*, 266:66–71, (Oct. 7, 1994).
J. Holt et al., "Growth retardation and tumour inhibition by BRCA1", *Nature Genetics*, 12:298–302, (Mar. 1996).
C. Szabo et al., "Inherited breast and ovarian cancer", *Hum. Mol. Genet.*, 4:1811–1817, (1995).
J. Hall et al., "Linkage of Early–Onset Familial Breast Cancer to Chromosome 17q21", *Science*, 250:1684–1689, (Dec. 21, 1990).
D. Easton et al., "Breast and Ovarian Cancer Incidence in BRCA1–Mutation Carriers", *Am. J. Hu. Genet.*, 56:265–271, (1995).
S. Narod et al., "An Evaluation of Genetic Heterogeneity in 145 Breast–Ovarian Cancer Families", *Am. J. Hu. Genet.*, 56:254–264, (1995).
S. Smith et al., "Allete losses in the region 17q12–21 in familial breast and ovarian cancer involve the wild–type chromosome", *Nature Genetics*, 2:128–131, (Oct. 1992).
P. Futreal et al., "BRCA1 Mutations in Primary Breast and Ovarian Carcinomas", *Science*, 266: 120–122, (Oct. 7, 1994).
D. Jensen et al., "BAP1: a novel ubiquitin hydrolase which binds to the BRCA1 RING finger and enhances BRCA1–mediated cell growth suppression", *Oncogene*, 16:1097–1112, (1998).
S. Merajver et al., "Somatic mutations in the BRCA1 gene in sporadic ovarian tumours", *Nature Genetics*, 9:439–433, (Apr. 1995).
R. Bienstock et al., "Molecular Modeling of the Amino–Terminal Zinc Ring Domain of BRCA1", *Cancer Res.*, 56:2539–2545, (Jun. 1, 1996).
R. Lovering et al., "Identification and preliminary characterization of a protein motif related to the zinc finger", *Proc. Nat'l Acad. Sci. USA*, 90:2112–2116, (Mar. 1993).
P. Freemont et al., "The RING Finger", *Ann. NY. Acad. Sci.*, 684:174–192, (1993).
A. Saurin, "Does this have a familiar RING?", *Trends in Biochem Sci.*, 21:208–214, (Jun. 1996).
L. Castilla et al., "Mutations in the BRCA1 gene in families with early–onset breast and ovarian cancer", *Nature Genet.*, 8:387–391, (Dec. 1994).
K. Borden et al., "The solution structure of the RING finger domain from the acute promyelocytic leukaemia proto–oncoprotein PML", *EMBO J.*, 14:1532–1541, (1995).
E. Koonin et al., "... Functional motifs...", *Nature Genet.*, 13: 266–268, (Jul. 1996).

Y. Chen et al., "Aberrant Subcellular Localization of BRCA1 in Breast Cancer", *Science*, 270: 789–791, (Nov. 3, 1995).
Y. Chen et al., "BRCA1 Is a 220–kDa Nuclear Phosphoprotein That Is Expressed and Phosphorylated in a Cell Cycle–dependent Manner", *Cancer Research*, 56:3168–3172, (Jul. 15, 1996).
R. Scully et al., "Association of BRCA1 with Rad51 in Mitotic and Mitotic Cells", *Cell*, 88:265–275, (Jan. 24, 1997).
M. Chapman et al., "Transcriptional activation by BRCA1", *Nature*, 382:678–679, (Aug. 22, 1996).
R. Scully et al., "BRCA1 is a component of the RNA polymerase II holoenzyme", *Proc. Nat'l. Acad. Sci. USA*, 94:5605–5610, (May 1997).
S. Marquis et al., "The developmental pattern of Brca1 expression implies a role in differentiation of the breast and other tissues", *Nature Genetics*, 11:17–26, (Sep. 1995).
J. Gudas et al., "Hormone–dependent Regulation of BRCA1 in Human Breast Cancer Cells", *Cancer Res.*, 55:4561–4565, (Oct. 15, 1995).
J. Gudas et al., "Cell Cycle Regulation of BRCA1 Messenger RNA in Human Breast Epithelial Cells", *Cell Growth and Differentiation*, 7:717–723, (1996).
J. Vaughn et al., "BRCA1 Expression Is Induced before DNA Synthesis in Both Normal and Tumor–derived Breast Cells", *Cell Growth and Differentiation*, 7:711–715, (Jun. 1996).
J. Marks et al., "BRCA1 expression is not directly responsive to estrogen", *Oncogene*, 14:115–121, (1997).
R. Hakem et al., "The Tumor Suppressor Gene Brca1 Is Required for Embryonic Cellular Proliferation in the Mouse", *Cell*, 85:1009–1023, (Jun. 28, 1996).
C. Liu et al., "Inactivation of the mouse Brca1 gene leads to failure in the morphogenesis of the egg cylinder in early postimplantation development", *Genes& Development*, 10:1835–1843, (1996).
V. Rao et al., "Antisense RNA to the putative tumor suppressor gene BRCA1 transforms mouse fibroblasts", *Oncogene*, 12:523–528, (1996).
M. Thompson et al., "Decreased expression of BRCA1 accelerates growth and is often present during sporadic breast cancer progression", *Nature Genetics*, 9:444–450, (Apr. 1995).
C. Chen et al., "The Nuclear Localization Sequences of the BRCA1 Protein Interact with the Importin–α Subunit of the Nuclear Transport Signal Receptor", *J. Biol. Chem.*, 271:32863–32868, (1996).
L. Wu et a l., "Identification of a RING protein that can interact in vivo with the BRCA1 gene product", *Nature Genetics*, 14:430–440, (Dec. 1996).
A. Klug et al., "Zinc fingers", *FASEB Journal*, 9:597–604, (May 1995).
J. Friedman et al., "KAP–1, a novel corepressor for the highly conserved KRAB repression domain", *Genes& Development*, 10:2067–2078, (1996).
S. Neuhausen & C. Marshall, "Loss of Heterozygosity in Familiar Tumors from Three BRCA1–linked Kindreds", *Cancer Res.*, 54:6069–6072, (Dec. 1, 1994).
J. Schildkraut et al., "Gynecology: Loss of Heterozygosity on Chromosome 17q11–21 in Cancers of Women Who Have Both Breast and Ovarian Cancer", *Am. J. Obstet. Gynecol.*, 172:908–913, (Mar. 1995).

M. FitzGerald et al., "Germ–Line BRCA1 Mutations in Jewish And Non–Jewish Women With Early–Onset Breast Cancer", *N. Engl. J. Med.*, 334:143–149, (1996).

D. Ford et al., "Risks of cancer in BRCA1–mutation carriers", *Lancet*, 343:692–695, (Mar. 19, 1994).

B. Rao et al., "Ashkenazi Jewish population frequencies for common mutations in BRCA1 and BRCA2", *Nature Genetics*, 14:185–187, (Oct. 1996).

J. Struewing et al., "The carrier frequency of the BRCA1 185delAG mutation is approximately 1 percent in Ashkenazi Jewish individuals", *Nature Genetics*, 11:198–200, (Oct. 1995).

R. Jensen et al., "BRCA1 is secreted and exhibits properties of a granin", *Nature Genetics*, 12:303–308, (Mar. 1996).

A. Bradley & S. Sharan, ". . . and secreted tumour suppressors", *Nature Genetics*, 13:268–271, (1996).

S. Zabludoff et al., "BRCA1 mRNA is expressed highly during meiosis and spermiogenesis but not during mitosis of male germ cells", *Oncogene*, 13:649–653, (1996).

* cited by examiner

FIG. 1A

```
hBRCA1:   1  MDLSAIRVEE VQNVINAMQK ILECPICLEL        IKEPVSTK C DHIFCKFCML KLLNQKK ---
mBRCA1:   1  MDLSAVQIQE VQNVLHAMQK ILECPICLEL        IKEPVSTK C DHIFCKFCML KLLNQKK ---
hRPT-1:  12                       EVTCPICLEL        IKEPVSAD C NHSFCRACIT LNYESNRNTD
hBARD1:  47                       LIRQSRQTNI        LREPVCLGGC EHIFQSNQVS DCI-------

*  *   *                                *  *    *
hBRCA1:   GFSQCPICKN DITKRSLQES TRFSQLVEEL LKIICAFQLD TGLE         100
mBRCA1:   GFSQCPICKN EITKRSLQGS TRGSQLAEEL LRINAAFELD TGHQ         100
hRPT-1:   GKGNCPFVCRV PYPFGNLRPM LHVANIVERL KGFKSIPEEQ KVNICAQHG    100
hBARD1:   GTG-CPVCYT P                                             89
           *   *
```

FIG. 2A

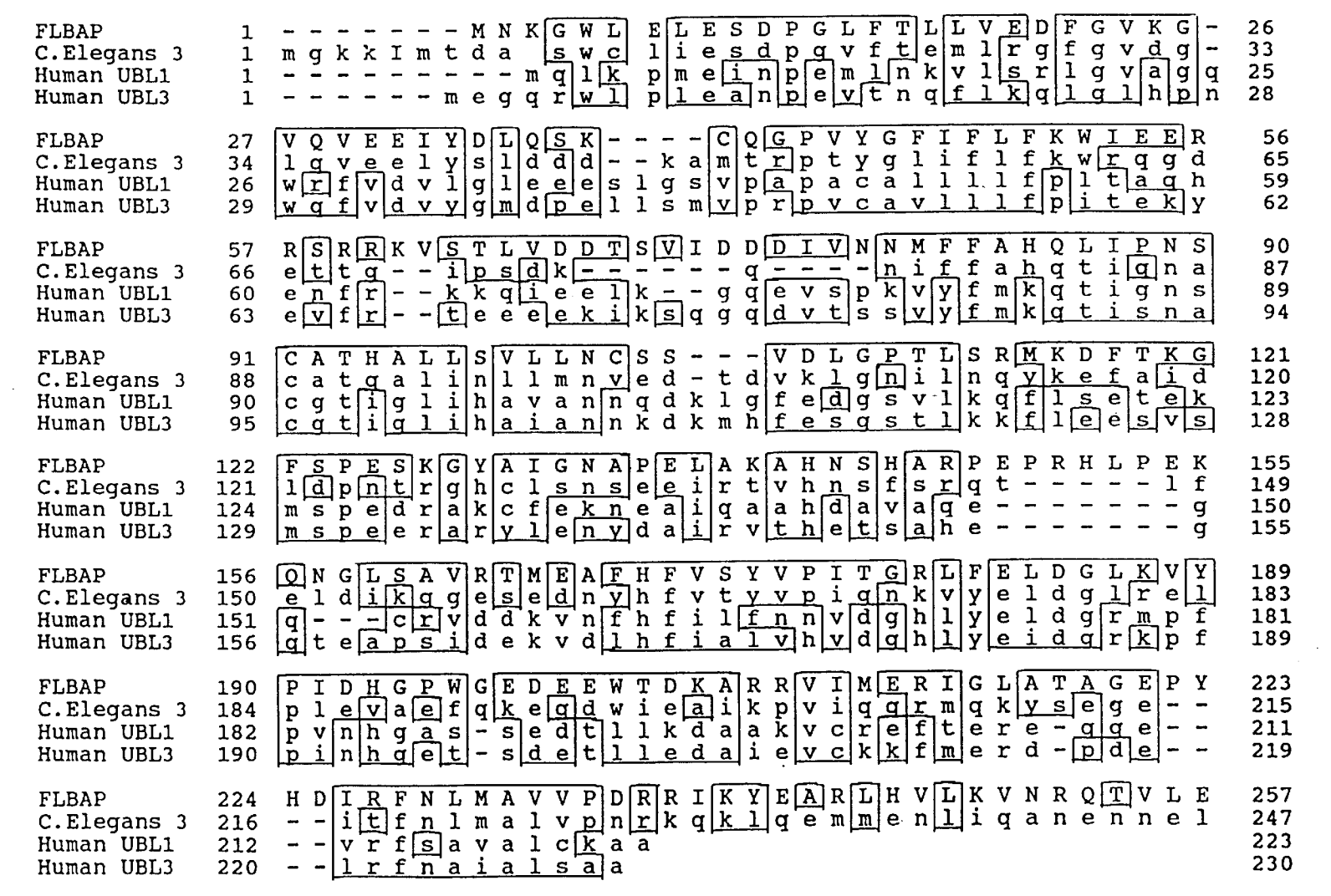

[Figure: Multiple sequence alignment of FLBAP, C.Elegans 3, Human UBL1, and Human UBL3 proteins showing conserved residues in boxed regions across positions 1-257.]

FIG. 2B

```
hBAP-1(483-729)     kkeiwnsdprghe------GPQPSPTPSNESTDTASEIGSAFNSPLRSPI
mBAP-1(518{del}718) ggidwipgyraqlr------------------------------------
mBAP-1(581-720)     ggidwipgvraqlrpls---------------------------------
mBAP-1(596-721)     ggidwipgyraqlrpls--------------------------------- hBAP-1(483-729)     RSANPTRPSSPVTSHISKVLFGEDDSLLRVDCIRYNRAVRDLGPVISTG
mBAP-1(518{del}718) -----RPSSPVTSHISKVLFGEDDSLLRVDCIRYNRAVRDLGPVISTG
mBAP-1(581-720)     ------------------------------------------------
mBAP-1(596-721)     ------------------------------------------------ hBAP-1(483-729)     LLHLAEDGVLSPLALTEGGKG SSPSIRPIQGSQGSS PVEKEVVE ATDS
mBAP-1(518{del}718) LLHLAEDGVLSPLALTEGGKG SSPSTR SSQGSQGSSGLEEKEVVE TES
mBAP-1(581-720)     ----------------------SSSPST RSSQGSQGSSGLEEKEVVE TES
mBAP-1(596-721)     -----------------------------SGLEEKEVVE TES hBAP-1(483-729)     R EKTGMVRSGEPLSGEKYSPKELLALLKCV EAEIANYEACLKEEVEKRK
mBAP-1(518{del}718) RDKPGLNRSSEPLSGEKYSPKELLALLKCA EAEIANYEACLKEEVEKRK
mBAP-1(581-720)     RDKPGLNRSSEPLSGEKYSPKELLALLKCA EAEIANYEACLKEEVEKRK
mBAP-1(596-721)     RDKPGLNRSSEPLSGEKYSPKELLALLKCV EAEIANYEACLKEEVEKRK hBAP-1(483-729)     KFKIDDQRRTHNYDEFICTFISMLAQEGMLANLVEQNISVRRRQGVSIG
mBAP-1(518{del}718) -KIDDQRRTHNYDEFICTFISMLAQEGMLANLVEQNISVRRRQGVSIG
mBAP-1(581-720)     KFKIDDQRRTHNYDEFICTFISMLAQEGMLANLVEQNISVRRRQGVSIG
mBAP-1(596-721)     KFKIDDQRRTHNYDEFICTFISMLAQEGMLANLVEQNISVRRRQGVSIG hBAP-1(483-729)     RLHKQRKPDRRKR SRPYKAKRQ*
mBAP-1(518{del}718) RLHKQRKPDRRKR ---msgr
mBAP-1(581-720)     RLHKQRKPDRRKR ---lsgr
mBAP-1(596-721)     RLHKQRKPDRRKR S------erpldr
```

FIGURE 3A

```
            GGCACGAGGC ATGGCGCTGA GGGGCCGCCC CGCGGGAAG ATG AAT           45
                                                      Met Asn
                                                       1

AAG GGC TGG CTG GAG CTG GAG AGC GAC CCA GGC CTC TTC ACC CTG            90
Lys Gly Trp Leu Glu Leu Glu Ser Asp Pro Gly Leu Phe Thr Leu
         5                   10                  15

CTC GTG GAA GAT TTC GGT GTC AAG GGG GTG CAA GTG GAG GAG ATC          135
Leu Val Glu Asp Phe Gly Val Lys Gly Val Gln Val Glu Glu Ile
         20                  25                  30

TAC GAC CTT CAG AGC AAA TGT CAG GGC CCT GTA TAT GGA TTT ATC          180
Tyr Asp Leu Gln Ser Lys Cys Gln Gly Pro Val Tyr Gly Phe Ile
         35                  40                  45

TTC CTG TTC AAA TGG ATC GAA GAG CGC CGG TCC CGG CGA AAG GTC          225
Phe Leu Phe Lys Trp Ile Glu Glu Arg Arg Ser Arg Arg Lys Val
         50                  55                  60

TCT ACC TTG GTG GAT GAT ACG TCC GTG ATT GAT GAT GAT ATT GTG          270
Ser Thr Leu Val Asp Asp Thr Ser Val Ile Asp Asp Asp Ile Val
         65                  70                  75

AAT AAC ATG TTC TTT GCC CAC CAG CTG ATA CCC AAC TCT TGT GCA          315
Asn Asn Met Phe Phe Ala His (Gln) Leu Ile Pro Asn Ser (Cys) Ala
         80                  85                  90

ACT CAT GCC TTG CTG AGC GTG CTC CTG AAC TGC AGC AGC GTG GAC          360
Thr His Ala Leu Leu Ser Val Leu Leu Asn Cys Ser Ser Val Asp
         95                 100                 105

CTG GGA CCC ACC CTG AGT CGC ATG AAG GAC TTC ACC AAG GGT TTC          405
Leu Gly Pro Thr Leu Ser Arg Met Lys Asp Phe Thr Lys Gly Phe
        110                 115                 120

AGC CCT GAG AGC AAA GGA TAT GCG ATT GGC AAT GCC CCG GAG TTG          450
Ser Pro Glu Ser Lys Gly Tyr Ala Ile Gly Asn Ala Pro Glu Leu
        125                 130                 135

GCC AAG GCC CAT AAT AGC CAT GCC AGG CCC GAG CCA CGC CAC CTC          495
Ala Lys Ala His Asn Ser His Ala Arg Pro Glu Pro Arg His Leu
        140                 145                 150

CCT GAG AAG CAG AAT GGC CTT AGT GCA GTG CGG ACC ATG GAG GCG          540
Pro Glu Lys Gln Asn Gly Leu Ser Ala Val Arg Thr Met Glu Ala
        155                 160                 165

TTC CAC TTT GTC AGC TAT GTG CCT ATC ACA GGC CGG CTC TTT GAG          585
Phe (His) Phe Val Ser Tyr Val Pro Ile Thr Gly Arg Leu Phe Glu
        170                 175                 180
```

FIGURE 3B

| | | | | | | | | | | | | | | |
|---|---|---|---|---|---|---|---|---|---|---|---|---|---|---|
| CTG | GAT | GGG | CTG | AAG | GTC | TAC | CCC | ATT | GAC | CAT | GGG | CCC | TGG | GGG | 630
| Leu | (Asp) | Gly | Leu | Lys | Val | Tyr | Pro | Ile | Asp | His | Gly | Pro | Trp | Gly |
| | | 185 | | | | 190 | | | | | 195 | | | |

```
CTG GAT GGG CTG AAG GTC TAC CCC ATT GAC CAT GGG CCC TGG GGG      630
Leu (Asp)Gly Leu Lys Val Tyr Pro Ile Asp His Gly Pro Trp Gly
    185                 190                 195

GAG GAC GAG GAG TGG ACA GAC AAG GCC CGG CGG GTC ATC ATG GAG      675
Glu Asp Glu Glu Trp Thr Asp Lys Ala Arg Arg Val Ile Met Glu
        200                 205                 210

CGT ATC GGC CTC GCC ACT GCA GGG GAG CCC TAC CAC GAC ATC CGC      720
Arg Ile Gly Leu Ala Thr Ala Gly Glu Pro Tyr His Asp Ile Arg
        215                 220                 225

TTC AAC CTG ATG GCA GTG GTG CCC GAC CGC AGG ATC AAG TAT GAG      765
Phe Asn Leu Met Ala Val Val Pro Asp Arg Arg Ile Lys Tyr Glu
        230                 235                 240

GCC AGG CTG CAT GTG CTG AAG GTG AAC CGT CAG ACA GTA CTA GAG      810
Ala Arg Leu His Val Leu Lys Val Asn Arg Gln Thr Val Leu Glu
        245                 250                 255

GCT CTG CAG CAG CTG ATA AGA GTA ACA CAG CCA GAG CTG ATT CAG      855
Ala Leu Gln Gln Leu Ile Arg Val Thr Gln Pro Glu Leu Ile Gln
        260                 265                 270

ACC CAC AAG TCT CAA GAG TCA CAG CTG CCT GAG GAG TCC AAG TCA      900
Thr His Lys Ser Gln Glu Ser Gln Leu Pro Glu Glu Ser Lys Ser
        275                 280                 285

GCC AGC AAC AAG TCC CCG CTG GTG CTG GAA GCA AAC AGG GCC CCT      945
Ala Ser Asn Lys Ser Pro Leu Val Leu Glu Ala Asn Arg Ala Pro
        290                 295                 300

GCA GCC TCT GAG GGC AAC CAC ACA GAT GGT GCA GAG GAG GCG GCT      990
Ala Ala Ser Glu Gly Asn His Thr Asp Gly Ala Glu Glu Ala Ala
        305                 310                 315

GGT TCA TGC GCA CAA GCC CCA TCC CAC AGC CCT CCC AAC AAA CCC     1035
Gly Ser Cys Ala Gln Ala Pro Ser His Ser Pro Pro Asn Lys Pro
        320                 325                 330

AAG CTA GTG GTG AAG CCT CCA GGC AGC AGC CTC AAT GGG GTT CAC     1080
Lys Leu Val Val Lys Pro Pro Gly Ser Ser Leu Asn Gly Val His
        335                 340                 345

CCC AAC CCC ACT CCC ATT GTC CAG CGG CTG CCG GCC TTT CTA GAC     1125
Pro Asn Pro Thr Pro Ile Val Gln Arg Leu Pro Ala Phe Leu Asp
        350                 355                 360

AAT CAC AAT TAT GCC AAG TCC CCC ATG CAG GAG GAA GAA GAC CTG     1170
Asn His Asn Tyr Ala Lys Ser Pro Met Gln Glu Glu Glu Asp Leu
        365                 370                 375
```

FIGURE 3C

| | | | | | | | | | | | | | | |
|---|---|---|---|---|---|---|---|---|---|---|---|---|---|---|
|GCG|GCA|GGT|GTG|GGC|CGC|AGC|CGA|GTT|CCA|GTC|CGC|CCA|CCC|CAG|1215
|Ala|Ala|Gly|Val|Gly|Arg|Ser|Arg|Val|Pro|Val|Arg|Pro|Pro|Gln|
| | |380| | | | |385| | | |390| | | |

CAG TAC TCA <u>GAT GAT GAG GAT GAC TAT GAG GAT GAC GAG GAG GAT</u> 1260
Gln Tyr Ser <u>Asp Asp Glu Asp Asp Tyr Glu Asp Asp Glu Glu Asp</u>
      395                          400                      405

<u>GAC</u> GTG CAG AAC ACC AAC TCT GCC CTT AGG TAT AAG GGG AAG GGA 1305
<u>Asp</u> Val Gln Asn Thr Asn Ser Ala Leu Arg Tyr Lys Gly Lys Gly
          410                      415                      420

ACA GGG AAG CCA GGG GCA TTG AGC GGT TCT GCT GAT GGG CAA CTG 1350
Thr Gly Lys Pro Gly Ala Leu Ser Gly Ser Ala Asp Gly Gln Leu
          425                      430                      435

TCA GTG CTG CAG CCC AAC ACC ATC AAC GTC TTG GCT GAG AAG CTC 1395
Ser Val Leu Gln Pro Asn Thr Ile Asn Val Leu Ala Glu Lys Leu
          440                      445                      450

AAA GAG TCC CAG AAG GAC CTC TCA ATT CCT CTG TCC ATC AAG ACT 1440
Lys Glu Ser Gln Lys Asp Leu Ser Ile Pro Leu Ser Ile Lys Thr
          455                      460                      465

AGC AGC GGG GCT GGG AGT CCG GCT GTG GCA GTG CCC ACA CAC TCG 1485
Ser Ser Gly Ala Gly Ser Pro Ala Val Ala Val Pro Thr His Ser
          470                      475                      480

<u>CAG</u> CCC TCA CCC ACC CCC AGC AAT GAG AGT ACA GAC ACG GCC TCT 1530
<u>Gln</u> Pro Ser Pro Thr Pro Ser Asn Glu Ser Thr Asp Thr Ala Ser
          485                      490                      495

GAG ATC GGC AGT GCT TTC AAC TCG CCA CTG CGC TCG CCT ATC CGC 1575
Glu Ile Gly Ser Ala Phe Asn Ser Pro Leu Arg Ser Pro Ile Arg
          500                      505                      510

TCA GCC AAC CCG ACG CGG CCC TCC AGC CCT GTC ACC TCC CAC ATC 1620
Ser Ala Asn Pro Thr Arg Pro Ser Ser Pro Val Thr Ser His Ile
          515                      520                      525

TCC AAG GTG CTT TTT GGA GAG GAT GAC AGC CTG CTG CGT GTT GAC 1665
Ser Lys Val Leu Phe Gly Glu Asp Asp Ser Leu Leu Arg Val Asp
          530                      535                      540

TGC ATA CGC TAC AAC CGT GCT GTC CGT GAT CTG GGT CCT GTC ATC 1710
Cys Ile Arg Tyr Asn Arg Ala Val Arg Asp Leu Gly Pro Val Ile
          545                      550                      555

AGC ACA GGC CTG CTG CAC CTG GCT GAG GAT GGG GTG CTG AGT CCC 1755
Ser Thr Gly Leu Leu His Leu Ala Glu Asp Gly Val Leu Ser Pro
          560                      565                      570

FIGURE 3D

```
CTG GCG CTG ACA GAG GGT GGG AAG GGT TCC TCG CCC TCC ATC AGA    1800
Leu Ala Leu Thr Glu Gly Gly Lys Gly Ser Ser Pro Ser Ile Arg
            575             580             585

CCA ATC CAA GGC AGC CAG GGG TCC AGC AGC CCA GTG GAG AAG GAG    1845
Pro Ile Gln Gly Ser Gln Gly Ser Ser Ser Pro Val Glu Lys Glu
            590             595             600

GTC GTG GAA GCC ACG GAC AGC AGA GAG AAG ACG GGG ATG GTG AGG    1890
Val Val Glu Ala Thr Asp Ser Arg Glu Lys Thr Gly Met Val Arg
            605             610             615

CCT GGC GAG CCC TTG AGT GGG GAG AAA TAC TCA CCC AAG GAG CTG    1935
Pro Gly Glu Pro Leu Ser Gly Glu Lys Tyr Ser Pro Lys Glu Leu
            620             625             630

CTG GCA CTG CTG AAG TGT GTG GAG GCT GAG ATT GCA AAC TAT GAG    1980
Leu Ala Leu Leu Lys Cys Val Glu Ala Glu Ile Ala Asn Tyr Glu
            635             640             645

GCG TGC CTC AAG GAG GAG GTA GAG AAG AGG AAG AAG TTC AAG ATT    2025
Ala Cys Leu Lys Glu Glu Val Glu Lys Arg Lys Lys Phe Lys Ile
            650             655             660

GAT GAC CAG AGA AGG ACC CAC AAC TAC GAT GAG TTC ATC TGC ACC    2070
Asp Asp Gln Arg Arg Thr His Asn Tyr Asp Glu Phe Ile Cys Thr
            665             670             675

TTT ATC TCC ATG CTG GCT CAG GAA GGC ATG CTG GCC AAC CTA GTG    2115
Phe Ile Ser Met Leu Ala Gln Glu Gly Met Leu Ala Asn Leu Val
            680             685             690

GAG CAG AAC ATC TCC GTG CGG CGG CGC CAA GGG GTC AGC ATC GGC    2160
Glu Gln Asn Ile Ser Val Arg Arg Arg Gln Gly Val Ser Ile Gly
            695             700             705

CGG CTC CAC AAG CAG CGG AAG CCT GAC CGG CGG AAA CGC TCT CGC    2205
Arg Leu His Lys Gln Arg Lys Pro Asp Arg Arg Lys Arg Ser Arg
            710             715             720

CCC TAC AAG GCC AAG CGC CAG TGAGGACTGC TGGCCCTGAC TCTGCAGCCC   2256
Pro Tyr Lys Ala Lys Arg Gln
            725

ACTCTTGCCG TGTGGCCCTC ACCAGGGTCC TTCCCTGCCC CACTTCCCCT         2306

TTTCCCAGTA TTACTGAATA GTCCAGCTG GAGAGTCCAG GCCCTGGGAA          2356

TGGGAGGAAC CAGGCCACAT TCCTTCCATC GTGCCCTGAG GCCTGACACG         2406

GCAGATCAGC CCCATAGTGC TCAGGAGGCA GCATCTGGAG TTGGGGCACA         2456

GCGAGGTACT GCAGCTTCCT CCACAGCCGG CTGTGGAGCA GCAGGACCTG         2506
```

FIGURE 3E

| | | | | | |
|---|---|---|---|---|---|
| GCCCTTCTGC | CTGGGCAGCA | GAATATATAT | TTTACCTATC | AGAGACATCT | 2556 |
| ATTTTTCTGG | GCTCCAACCC | AACATGCCAC | CATGTTGACA | TAAGTTCCTA | 2606 |
| CCTGACTATG | CTTTCTCTCC | TAGGAGCTGT | CCTGGTGGGC | CCAGGTCCTT | 2656 |
| GTATCATCCA | CGGTCCCAAC | TACAGGGTCC | TAGCTGGGGG | CCTGGGTGGG | 2706 |
| CCCTGGGCTC | TGGGCCCTGC | TGCTCTAGCC | CCAGCCACCA | GCCTGTCCCT | 2756 |
| GTTGTAAGGA | AGCCAGGTCT | TCTCTCTTCA | TTCCTCTTAG | GAGAGTGCCA | 2806 |
| AACTCAGGGA | CCCAGCACTG | GGCTGGGTTG | GGAGTAGGGT | GTCCCAGTGG | 2856 |
| GGTTGGGGTG | AGCAGGCTGC | TGGGATCCCA | TGGCCTGAGC | AGAGCATGTG | 2906 |
| GGAACTGTTC | AGTGGCCTGT | GAACTGTCTT | CCTTGTTCTA | GCCAGGCTGT | 2956 |
| TCAAGACTGC | TCTCCATAGC | AAGGTTCTAG | GGCTCTTCGC | CTTCAGTGTT | 3006 |
| GTGGCCCTAG | CTATGGGCCT | AAATTGGGCT | CTAGGTCTCT | GTCCCTGGCG | 3056 |
| CTTGAGGCTC | AGAAGAGCCT | CTGTCCAGCC | CCTCAGTATT | ACCATGTCTC | 3106 |
| CCTCTCAGGG | GTAGCAGAGA | CAGGGTTGCT | TATAGGAAGC | TGGCACCACT | 3156 |
| CAGCTCTTCC | TGCTACTCCA | GTTTCCTCAG | CCTCTGCAAG | GCACTCAGGG | 3206 |
| TGGGGACAG | CAGGATCAAG | ACAACCCGTT | GGAGCCCCTG | TGTTCCAGAG | 3256 |
| GACCTGATGC | CAAGGGGTAA | TGGGCCCAGC | AGTGCCTCTG | GAGCCCAGGC | 3306 |
| CCCAACACAG | CCCCATGGCC | TCTCCAGATG | GCTTTGAAAA | GGTGATCCAA | 3356 |
| CAGGCCCCTT | TATCTGTACA | TAGTGACTGA | GTGGGGGGTG | CTGGCAAGTG | 3406 |
| TGGCACTCCT | CTGGGCTGAG | CACAGCTTGA | CCCCTCTAGC | CCCTGTAAAA | 3456 |
| CTGGATCAAT | GAATGAATAA | AACTCTCCTA | AGATCTCCTG | AGAAAAAAAA | 3506 |
| AAAAAAAAG | G | | | | 3517 |

FIG. 3F

| | | | |
|---|---|---|---|
| BAP1 | 1 | -------MNKGWLELESDPGLFTLLVEDFGVKG-VQVEEIYDLQS-- | 37 |
| CAEEL-C08B11.7 | 1 | MGKKIMTDAGSWCLIESDPGVFTEMLRGFGVDG-LQVEELYSLDD-- | 44 |
| UCH-DROME | 1 | -------MLTWTPLESNPEVLTKYIHKLAVSPAWSVTDVIGLED-D | 38 |
| YUH1 | 1 | ----MSGENRAVVPIESNPEVFTNFAHKLGLKNEWAYFDIYSLTEPE | 43 |
| UCH-L3 | 1 | ------MEGQRWLPLEANPEVTNQFLKQLGLHPNWQFVDVYGMDP-E | 48 |
| UCH-L1 | 1 | ---------MQLKPMEINPEMLNKVLSRLGVAGQWRFVDVLGLEE-E | 37 |
| BAP1 | 38 | KC---QGPVYGFIFLFKWIEERRSRRKVSTLVDDTSVIDDDIVNNMF | 81 |
| CAEEL-C08B11.7 | 45 | -DKAMTRPTYGLIFLFKWRGDE----TTGIP-------SDKQNIF | 78 |
| UCH-DROME | 39 | TLEWIPRPVKAFILLFPCSETYEKHR--TEEHDRIKEVEEQHPEDLF | 83 |
| YUH1 | 44 | LLAFLPRPVKAIVLLFPINEDRKSST--SQQIT-------SSYDVI | 88 |
| UCH-L3 | 41 | LLSMVPRPVCAVLLLFPITEKYEVFR--TEEEEKIKSQGDVTSSVY | 85 |
| UCH-L1 | 38 | SLGSVPAPACALLLLFPLTAQHENFR--KKQIEELK--GQEVSPKVY | 80 |
| BAP1 | 82 | FAHQLIPNSCATHALLSVLLNCSS--VD-LGPTLSRMKDFTKGFSP- | 124 |
| CAEEL-C08B11.7 | 79 | FAHQTIQNACATQALINLLMNVED-TDVKLGNILNQYKEFAIDLDP- | 123 |
| UCH-DROME | 84 | YMRQFTENACGTVALIHSVANNKE-VDIDRG-VLKDFLEKTASLSP- | 127 |
| YUH1 | 81 | WFKQSVKNACGLYAILHSLSNNQS--LLEPGSDLDNFLKSQSDTSSS | 125 |
| UCH-L3 | 86 | FMKQTISNACGTIGLIHAIANNKDKMHFESGSTLKKFLEESVSMSP- | 131 |
| UCH-L1 | 81 | FMKQTIGNSCGTIGLIHAVANNQDKLGFEDGSVLKQFLSETEKMSP- | 126 |
| BAP1 | 125 | ESKGYAIGNAPELAKAHSHARPEPRHLPEKQNGLSAVRTMEAFHFV | 171 |
| CAEEL-C08B11.7 | 124 | NTRGHCLSNSEEIRTVHNSFSR----QTLFELDIKGGESEDNYHFV | 165 |
| UCH-DROME | 128 | EERGRALEKDEKFTADHEALAQ-------EGQ-TNAANHEKVIHFI | 166 |
| YUH1 | 126 | KNRFDDVTTDQFVLNVIKENVQT----FSTGQSEAPEATADTNLHYI | 168 |
| UCH-L3 | 132 | EERARYLENYDAIRVTHETSAH------EGQTEAPSIDEKVDLHFI | 171 |
| UCH-L1 | 127 | EDRAKCFEKNEAIQAAHDAVAQ------EGQ--CR-VDDKVNFHFI | 163 |
| BAP1 | 172 | SYVPITGRLFELDGL-KVYPIDHG---PWGEDEEWTDKARRVIMERI | 214 |
| CAEEL-C08B11.7 | 166 | TYVPIGNKVYELDGL-RELPLEVA---EFQKEQDWIEAIKPVIQQRM | 208 |
| UCH-DROME | 167 | ALVNKEGTLYELDGR-KSFPIKHG---PTSEE-TFVKDAAKVCKEFM | 208 |
| YUH1 | 169 | TYVEENGGIFELDGRNLSGPLYLGKSDPTATD-LIEQELVRVRVASY | 214 |
| UCH-L3 | 172 | ALVHVDGHLYELDGR-KPFPINHG---ETSDE-TLLEDAIEVCKKFM | 213 |
| UCH-L1 | 164 | LFNNVDGHLYELDGR-MPFPVNHG---ASSED-TLLKDAAKVCREFT | 205 |
| BAP1 | 215 | GLATAGEPYHDIRFNLMAVVPDRRIKYEARLHVLKVNRQTVLEALQQ | 261 |
| CAEEL-C08B11.7 | 209 | QKYSEGE----ITFNLMALVPNRKQKLQEMMENLIQANENNELEEQI | 251 |
| UCH-DROME | 209 | ARD-PNE----VRFTVLALTAAQQ | 227 |
| YUH1 | 215 | MEN-ANEED-VLNFAMLGLGPNWE | 236 |
| UCH-L3 | 214 | ERD-PDE----LRFNAIALSAA | 238 |
| UCH-L1 | 206 | ERE-QGE----VRFSAVALCKAA | 223 |

| | | | |
|---|---|---|---|
| BAP1 | 630 | KELLALLKCVEAEIANYEACLKEEVEKRKKFKID | 663 |
| CAEEL-C08B11.7 | 238 | LIQANENNELEEQIADLNKAIADEDYKMEMYRKE | 271 |
| BAP1 | 634 | DQRRTHNYDEFICTFISMLAQEGMLANLVEQNIS | 667 |
| CAEEL-C08B11.7 | 272 | NNRRHNYTPFVIELMKILAKEGKLVGLVDNAYQ | 305 |
| BAP1 | 668 | VRRRQGVSIGRLHKQRKPDRRKRSRPYKAKRQ | 729 |
| CAEEL-C08B11.7 | 306 | AAK-EK-S--KLNTDITKLELKRKQ | 326 |

BRCA1 ASSOCIATED POLYNUCLEOTIDE (BAP-1) AND USES THEREFOR

CROSS-REFERENCE TO RELATED APPLICATIONS

This application is a 35 USC §371 of International Patent Application No. PCT/US97/13684, filed Jul. 30, 1997, which claims the benefit of the priority dates of U.S. Provisional Patent Application No. 60/038,109, filed Feb. 19, 1997, now abandoned and U.S. Provisional Patent Application No. 60/022,997, filed Aug. 2, 1996, now abandoned.

This invention was made under work supported by National Institutes of Health, Grant Nos. CA52009, DK49210, and TM54220. The United States Government has certain rights in this invention.

FIELD OF THE INVENTION

This invention relates generally to the field of genes associated with cancers, and particularly, to BRCA1.

BACKGROUND OF THE INVENTION

The breast and ovarian cancer susceptibility gene, BRCA1, is linked to the hereditary form of breast cancer. The BRCA1 gene is located on chromosome 17 at the locus 17q21 and encodes a protein of 1863 amino acids. The BRCA 1 locus spans >100 kb comprising 24 exons [Miki et al, *Science*, 266:66–71 (1994)]. Expression of wild-type BRCA 1 inhibits colony function and tumor growth in vivo, whereas tumor derived mutations of BRCA 1 abolish this growth suppression [Holt et al, *Nature Genetics*, 12:298–302 (1996)]. Germline mutations in BRCA 1 appear to account for 50% of familial breast cancers and essentially all families with 17q21-linked inherited susceptibility to ovarian and breast cancer [Szabo et al, *Hum. Mol. Genet.*, 4:1811–1817 (1995); Hall et al, *Science*, 250:1684–1689 (1990); Easton et al, *Am. J. Hu. Genet.*, 56:265–271 (1995); Narod et al, *Am. J. Hu. Genet.*, 56:254–264 (1995)]. Kindreds segregating constitutive BRCA1 mutations show a lifetime risk of 40–50% for ovarian cancer and >80% for breast cancer [Easton et al, *Am. J. Hum. Genet.*, 52:678–701 (1993); Easton et al, *Am. J. Hum. Genet.*, 56:265–271 (1995)].

The classification of BRCA 1 as a highly penetrant, autosomal dominant tumor suppressor gene has been genetically confirmed by the finding of frequent loss or mutation (LOH) of the wild-type allele in breast tumors from mutation carriers [Hall et al, *Science*, 250:1684–1689 (1990); Miki et al, cited above; Smith et al, *Nature Genetics*, 2:128–131 (1992)]. Surprisingly, BRCA 1 mutations in sporadic breast cancer including those which show LOH have yet to be found and are extremely rare in sporadic ovarian cancer [Futreal et al, *Science*, 266:120–122 (1994); Merajver et al, *Nature Genetics*, 9:439–443 (1995)].

Although the BRCA1 protein resembles no known protein, it does contain a RING domain at its amino terminus [Miki, cited above; Bienstock et al, *Cancer Res.*, 56:2539–2545 (1996)]. The RING finger domain is a complicated structure which chelates two zinc atoms using 7 Cys residues and 1 His residue [$C_3HC_4$; Lovering et al, *Proc. Natl. Acad. Sci. USA*, 90:2112–2116 (1993); Freemont et al, *Ann. NY Acad. Sci.*, 684:174–192 (1993)]. This domain is present in a wide variety of proteins with various functions, but the function of the RING finger domain within these proteins is unknown [for a review see Saurin, *Trends in Biochem. Sci.*, 21:208–214 (1996)]. The RING finger of BRCA1 is important to its function since missense mutations in the RING domain (Cys61Gly and Cys64Gly) are found in breast/ovarian kindreds [Friedman et al, *Nat. Genet.*, 8:399–404 (1994); Merajver, cited above; Castilla et al, *Nature Genet.*, 8:387–391 (1994)]. In addition, the RING finger domain is the most conserved region of BRCA1, when comparing the human, mouse and rat proteins. The BRCA1 RING finger is anticipated to be a binding site for protein(s) which either mediate BRCA1 tumor suppressor function or serve to regulate these functions. Genetic evidence supports this in that single amino-acid substitutions at metal chelating cysteines, C61G and C64G, occur in kindreds; these mutations segregate with the disease susceptibility phenotype and are predicted to abolish RING finger structure.

Other functions of BRCA1 are discussed in the following references which are incorporated herein by reference: Borden et al, *EMBO J.*, 14:1532–1541 (1995); Lovering et al, *Proc. Natl. Acad. Sci. USA*, 90:2112–2116 (1993); Koonin et al, *Nature Genet.*, 13:266–268 (1996); Chen et al, *Science*, 270:789–791 (1995); Chen et al, *Cancer Research*, 56:3168–3172 (1996); Scully et al, *Science*, 272:123–126 (1996); Thakur et al, *Molecular & Cellular Biology*, 17:444–452 (1997); Scully et al, *Cell*, 88:265–275 (1997); Chapman et al, *Nature*, 382:678–679 (1996); Scully et al, *Proc. Natl. Acad. Sci. USA*, 94:5605–5610 (1997); Marquis et al, *Nature Genetics*, 11:17–26 (1995); Gudas et al, *Cancer Res.*, 55:4561–4565 (1995); Gudas et al, *Cell Growth and Differentiation*, 7:717–723 (1996); Vaughn et al, *Cell Growth and Differentiation*, 7:711–715 (1996); Marks et al, *Oncogene*, 14:115–121 (1997); Zabludoff et al, *Oncogene*, 13:649–653 (1996); Hakem et al, *Cell*, 85:1009–1023 (1996); Liu et al, *Genes & Development*, 10:1835–1843 (1996); Rao et al, *Oncogene*, 12:523–528 (1996); Thompson et al, *Nature Genetics*, 9:444–450 (1995); Chen et al, *J. Biol. Chem.*, 271:32863–32868 (1996); Wu et al, *Nature Genetics*, 14:430–440 (1996); Klug et al, *FASEB Journal*, 9:597–604 (1995); Saurin et al, *Trends in Biochem. Sci.*, 21:208–214 (1996); Friedman et al, *Genes & Development*, 10:2067–2078 (1996); Neuhausen & Marshall, *Cancer Res.*, 54:6069–6072 (1994); Schildkraut et al, *Am. J. Obstet. Gynecol.*, 172:908–913 (1995); FitzGerald et al, *N. Engl. J. Med.*, 334:143–149 (1996); Ford et al, *Lancet*, 343:692–695 (1994); Muto et al, *Cancer Research*, 56:1250–1252 (1996); Rao et al, *Nature Genetics*, 14:185–187 (1996), Struewing et al, *Nature Genetics*, 11:198–200 (1995); Couch et al, *Human Mutation*, 8:8–18 (1996); Holt et al, *Nature Genetics*, 12:298–302 (1996); Jensen et al, *Nature Genetics*, 12:303–308 (1996); Bradley & Sharan, *Nature Genetics*, 13:268–271 (1996).

There is a need in the art for compositions and methods useful in the treatment and/or prophylaxis of cancers caused by loss of, and mutations in, BRCA1.

SUMMARY OF THE INVENTION

The present invention meets the needs in the art by identifying a novel mammalian BRCA1 Associated Protein (BAP-1) and nucleic acid sequences encoding same. BAP1 is the first nuclear-localized ubiquitin carboxy-terminal hydrolase to be identified and is a new tumor suppressor gene which functions in the BRCA1 growth control pathway. Compositions, both diagnostic and therapeutic, based on this newly identified protein are provided herein.

Thus, in one aspect, the present invention provides a nucleic acid sequence, which is isolated from cellular materials with which it is naturally associated. The nucleic acid sequence is preferably selected from SEQ ID NO:1, or a fragment thereof. Such a fragment may have a specified biological function as discussed below, or may encode a peptide having a similar biological function as the intact BAP-1. Homologous nucleotide sequences, and modified nucleotide sequences which encode peptides or proteins which have a similar biological function as the intact BAP-1, are also included in this aspect of the invention.

In another aspect, the present invention provides a mammalian BRCA1 associated protein (BAP-1). In one preferred embodiment, the protein is human and has the amino acid sequence of SEQ ID NO:2. In another embodiment a fragment of the SEQ ID NO:2 encodes a peptide having a similar biological function as the intact BAP-1 protein. Amino acid sequences homologous to SEQ ID NO: 2, and modified amino acid sequences of SEQ ID NO: 2, which encode peptides or proteins which have a similar biological function as the intact BAP-1 or a specified biological function as discussed below, are also included in this aspect of the invention.

In yet another aspect, the present invention provides a polynucleotide molecule, for example, a vector or plasmid, that comprises a mammalian BAP-1 nucleic acid sequence as defined herein under the control of suitable sequences which direct and regulate expression of the BAP-1 nucleic acid sequence.

In a further aspect, the present invention provides a host cell transformed with a polynucleotide molecule or vector of the invention.

In yet a further aspect, the present invention provides a method of recombinantly expressing BAP-1 or a peptide fragment thereof, by culturing a recombinant host cell according to the invention under conditions which permit expression of BAP-1 or a fragment thereof.

In still a further aspect, the present invention provides an anti-BRCA1 associated protein (BAP-1) antibody.

In yet another aspect, the invention provides a diagnostic reagent comprising an antibody of the invention and a detectable label. Alternatively, a diagnostic reagent of the invention may comprise a nucleic acid sequence of the invention, or a fragment thereof, and a detectable label which is associated with said sequence.

In still another aspect, the invention provides a method of detecting a cancer associated with abnormal levels of BAP-1 comprising providing a biopsy sample from a patient suspected of having said cancer and incubating said sample in the presence of a diagnostic reagent of the invention.

In a further aspect, the present invention provides methods of identifying compounds which specifically bind to BAP-1 or a fragment thereof. In still a further aspect, the present invention provides for compounds or drugs produced by use of the above methods.

Other aspects and advantages of the present invention are described further in the following detailed description of the preferred embodiments thereof.

BRIEF DESCRITION OF THE DRAWINGS

FIG. 1A illustrates the structural features of the BRCA1 gene product. It shows an alignment of RING finger domains of human BRCA1 [SEQ ID NO:3] and mouse BRCA1 [SEQ ID NO:4] (AA1–100), RPT-1 (amino acids 12–100 of SEQ ID NO:5), a putative lymphocyte specific transcription factor having the most closely related RING finger, and BARD1 (AA 47–89) [SEQ ID NO: 19]. Asterisks (*) identify the Zn-chelating amino acids that form the core of the RING finger. Boxed amino acids show regions of identity between the RING finger domains of human BRCA1 and the other proteins. Alignment was performed by ClustalW [Thompson et al, *Nucleic Acids Research*, 22:4673–4680 (1994)].

FIG. 1B is a schematic map which illustrates the constructs made when the amino terminal 100 amino acids of human BRCA1 (which includes the RING finger domain) and the indicated amino acids of the various BRCA1-RF mutants and controls (described in Example 1) were fused to the LexA DNA-binding domain. The signature C3HC4 structure is highlighted.

FIG. 2A provides a comparison of the amino terminal regions of BAP-1 (FLBAP) [amino acids 1–257 of SEQ ID NO: 2], a C. elegans 3 protein [SEQ ID NO: 16], and human ubiquitin carboxyl-terminal hydrolase isozymes L1 (human UBL1) [SEQ ID NO: 17] and L3 (human UBL3) [SEQ ID NO: 18]. Boxed regions indicate areas of greater than 85% homology. This region contains the active sites of UBL1 and UBL3.

FIG. 2B illustrates the sequences and provides a comparison of the partial human [SEQ ID NO: 6] and mouse BAP-1 proteins [SEQ ID NO: 7–9] isolated via the yeast 2-hybrid screens of Example 2. Capital letters encode BAP-1. Lower case letters represent the amino acids encoded by the vector. Human BAP-1 is fused to Gal4 activation domain. Mouse BAP-1 is fused to the VP16 activation domain.

FIGS. 3A–3E provide the nucleic acid [SEQ ID NO:1] and amino acid [SEQ ID NO:2] sequences of the novel ubiquitin carboxy-terminal hydrolase, BAP-1. The longest open reading frame which contained the amino acids defined by the (human) 2-hybrid fusion protein is 2188 nucleotides encoding 729 amino acids. The cDNA also contains 39 nucleotides of 5'UTR and 1705 nucleotides of 3'UTR. The enzymatic active site is contained within the first 250 amino acids; the active site residues are circled. The putative nuclear localization signals (NLS) are underlined, the highly acidic region is boxed with heavy lines, the interaction domain is boxed and the protein fragment used to generate BAP1 polyclonal antibodies is bracketed (A.A.'s 483–576 of SEQ ID NO: 2). The conserved amino acids of the ubiquitin COOH-terminal hydrolase active site consensus are circled (amino acids 91, 169, 184 of SEQ ID NO: 2).

FIG. 3F is a comparison of BAP1 (amino acids 1–261 of SEQ ID NO: 2) with other UCH's. UCH-CAEEL (genbank #Q09444) (amino acids 1–251 of SEQ ID NO: 20), UCH DROME (genbank #P35122) [SEQ ID NO: 21] (aa 1–227), YUH1 (genbank #P35127) [SEQ ID NO: 22] (aa 1–236), UCHL-1 (genbank #P09936) [SEQ ID NO: 24] (aa 1–223), UCHL-3 (genbank #P15374) [SEQ ID NO: 23] (aa 1–230). BAP1 (amino acids 630–729 of SEQ ID NO: 2) is further compared to CAEEL-CO8B11.7 (amino acids 238–326 of SEQ ID NO: 20). The BLAST search algorithm was used to identify proteins closely related to BAP1 [Altschul et al, *J. Mol. Biol.*, 215:403–410 (1990)]. The UCH domain of four of these proteins were aligned with BAP1 using the CLUSTALW (ver.1.6) algorithm [Thompson et al, cited above]. Areas of homology with other UCH's are boxed. Only CAEEL-CO8B11.7 showed any homology outside of the enzymatic region.

Figure 3G:
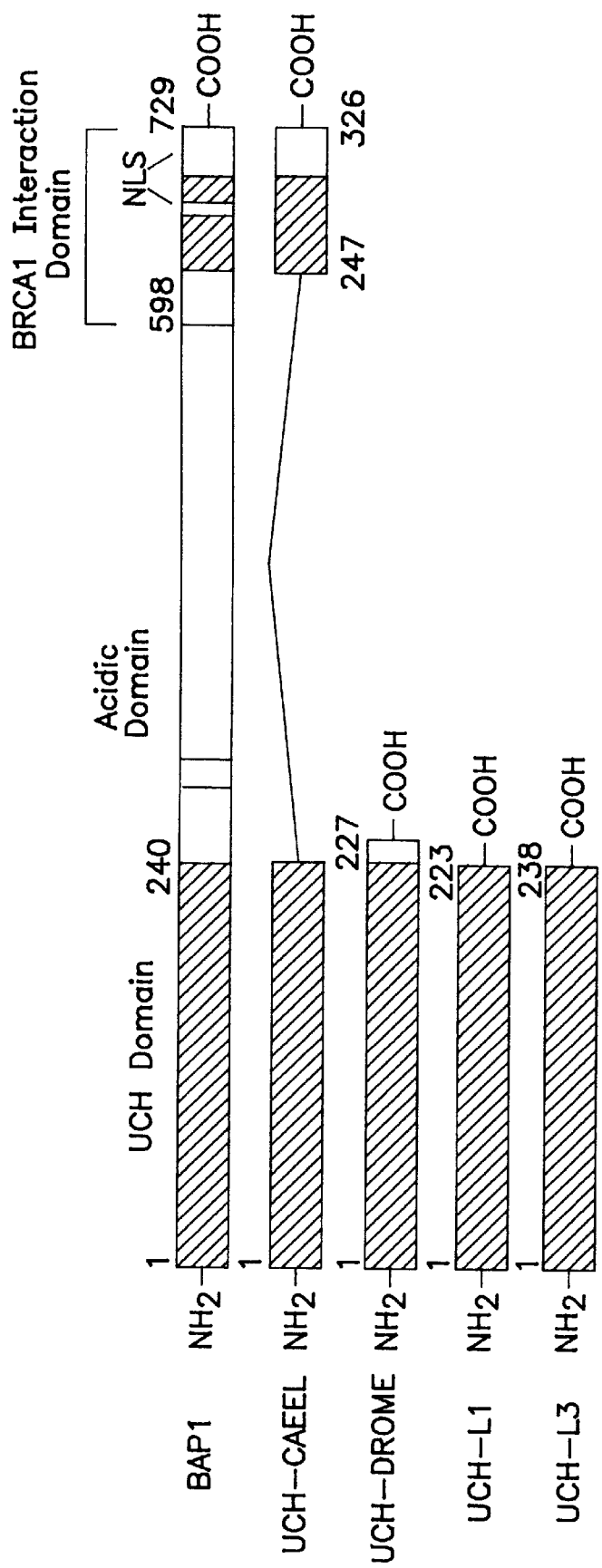

FIG. 3G is a schematic comparison of the BAP1 and UCH's. The region necessary for the interaction with BRCA1 (AAs 598–729) is indicated in the diagrams with light crosshatching.

DETAILED DESCRIPTION OF THE INVENTION

The present invention provides a novel protein, BRCA1 associated protein-1 (BAP1). BAP1 is a novel, nuclear localized, enzyme which displays the signature motifs and activities of a ubiquitin carboxy-terminal hydrolase, i.e., BAP1 cleaves model ubiquitin substrates in vitro. In fact, BAP1 is the first nuclear-localized ubiquitin carboxy-terminal hydrolase to be identified. The ubiquitin hydrolase function of BAP1 implicates the ubiguitin-proteasome pathway in either the regulation, or as a direct effector, of BRCA1 function. Thus, BAP1 likely has a broad role in ubiquitin-dependent regulatory processes within the nucleus, including the emerging role of ubiquitin conjugation as a subcellular targeting signal, as well as in transcription, chromatin remodeling, cell cycle control and DNA repair/recombination.

BAP1 also enhances the tumor growth suppression properties of BRCA1 in colony formation assays and does so in a manner dependent upon the UCH enzymatic domain and the BRCA1-interaction domain. BAP1 specifically binds to the wild-type BRCA1 RING finger domain (BRCA1-RF) both in vitro and in vivo, but not to mutant BRCA1-RF's, e.g., the C61G or C64G mutated RING fingers found in tumors from breast cancer kindreds or other closely related RING fingers. The interaction between BAP1 and BRCA1 occurs in vitro and BAP1 mRNA is expressed in those tissues which also express BRCA1. Thus, BAP1 has a role as a tumor suppressor gene.

As described below, the yeast two-hybrid system was employed to isolate mouse and human clones of BAP1. The human BAP1 locus was mapped to human chromosome 3p21.3. Rearrangements and intragenic homozygous deletions and mutations of BAP1 have been found in lung carcinomas, including homozygous deletions found in non-small cell lung cancers.

Together, this evidence supports the role of BAP1 as a tumor suppressor gene and as a regulator or an effector in BRCA1 growth control pathways. Both the specificity of the BRCA1 RING finger-BAP1 interaction and the fact that independent, tumor-derived missense mutations in the cysteines in the BRCA1 RING finger domain abolish interaction with BAP1 provide compelling evidence for the physiological relevance of this interaction.

The invention further provides nucleic acid sequences which encode BAP1 or fragments of BAP1 which have a biological function, diagnostic and therapeutic reagents, as well as methods of using BAP1, its nucleic acid sequences, and antibodies developed thereto. The nucleic acid sequences, protein, amino acid sequences and antibodies directed to BAP1 are useful in the detection, diagnosis and treatment of cancers associated with inappropriate BAP-1 levels and/or loss of chromosomal region 3p21.

In one embodiment, the nucleic acid sequence of the invention is an about 3.5 kb cDNA [SEQ ID NO: 1], encoding BAP-1. BAP-1 is a 729 amino acid protein [SEQ ID NO: 2] which interacts through its carboxy terminus with the BRCA1 RING finger domain. In addition to containing the 250 amino acid amino terminal UCH catalytic domain, it includes a long carboxy-terminal extension with rich in proline, serine and threonine and and contains a short region of extreme acidity in which 12 of 13 amino acids are either Glu or Asp, elements which may confer a short half-life upon the protein [Rechsteiner et al, *Trends Biochem. Sci.*, 21:267–271 (1996)]. The extreme carboxy-terminus encodes two potential nuclear localization signals which overlap the approximately 125 amino acid BRCA1-interaction domain. It was this domain that was independently isolated from mouse and human libraries in the two-hybrid screen of Example 2 and is predicted to fold into a long amphipathic helix of coiled-coil character, the structure of which may be important for BRCA1 interaction. Truncation into this region or substitution of a proline for leucine 691 abolish the BAP1-BRCA1 interaction. A potential splice variant in BAP1 results in loss of 31 amino acids of the BRCA1 interaction domain and greatly reduces the ability of BAP1 to bind the BRCA1 RING finger, further suggesting that the BAP1-BRCA1 interaction is regulated. Thus, the BAP1 carboxy-terminus is tethered to BRCA1 via the RING finger domain and that the UCH catalytic domain is free to interact with ubiquitin substrates.

Northern analysis showed that BAP-1 is a ~4 kb mRNA expressed in a variety of tissues and cell lines. The cDNA encodes a protein of 80 kD predicted molecular weight. However, expression of the cDNA in vitro or in COS1 cells generated a protein with an apparent molecular weight of approximately 91 kDa suggesting possible post-translational modifications. Localization of BAP-1 by cell fractionation indicated that it is predominantly a nuclear protein. Chromosomal analysis by fluorescent in situ hybridization (FISH) localized BAP-1 to chromosome 3p21, a genomic region found to be deleted in some breast cancers. The loss of BAP-1 function, individually or in tandem with BRCA1, is anticipated to be associated with breast cancer progression. Thus, the BAP-1 protein may mediate BRCA1 function and inhibit its oncogenic activity. These and other aspects of the invention are discussed in more detail below.

BRCA1 is likely a direct substrate for the UCH activity of BAP1. Thus, in contrast to all of the known UCHs which are comprised entirely of the UCH domain, the carboxy-terminal extension of BAP1 provides substrate and/or targeting specificity for the catalytic function. Regulated ubiquitination of BRCA1 and subsequent proteasome-mediated degradation would not be surprising given that both BRCA1 levels and subnuclear localization are tightly regulated in the mitotic cell-cycle and during meiosis [Gudas et al, cited above; Scully et al, cited above; Zabludoff et al, cited above]. BAP1-mediated deubiquitination of BRCA1 would be expected to stabilize the protein and protect it from proteasome-mediated degradation. This is consistent with both the ability of co-transfected BAP1 to enhance the tumor suppressor effects of BRCA1 in colony formation assays and the finding of mutations in BAP1 in cancer cell lines.

The BRCA1-BAP1 association may also serve to target the UCH domain to other substrates. These substrates may be bound to other sites on BRCA1. BRCA1 could be construed as an assembly or scaffold molecule for regulated assembly of multiprotein complexes, a function which has been postulated for other tumor suppressor proteins [e.g. pRb; Sellers et al, *Biochim. Biophys. Acta.*, 1288:M1–5 (1996); Welch et al, *Genes Dev.*, 9:31–46 (1995)]. BAP1 may thus be a regulator of this assembly via controlled ubiquitin proteolysis, similar to two other RING finger-containing proteins involved in controlled proteolysis processes, i.e., a mouse homologue of the drosophila seven-in-absentia (siah; a RING finger protein) and the herpes virus protein VMW110 RING finger protein [Everett et al, *EMBO J.*, 16:566–577 (1997)].

The following description defines the aspects of this invention in more detail.

I. Nucleic Acid Sequences

The present invention provides mammalian nucleic acid sequences encoding BAP-1. The nucleic acid sequences of this invention are isolated from cellular materials with which they are naturally associated. In one embodiment, a BAP-1 cDNA sequence is provided in SEQ ID NO:1 (FIGS. 3A–3E).

Given the cDNA sequences of SEQ ID NO: 1, one of skill in the art can readily obtain the corresponding anti-sense strands of these DNA sequences. Further, using known techniques, one of skill in the art can readily obtain genomic sequences corresponding to these DNA sequences or the corresponding RNA sequences, as desired.

Similarly the availability of SEQ ID NO: 1 of this invention permits one of skill in the art to obtain other species BAP-1 analogs, by use of the nucleic acid sequences of this invention as probes in a conventional technique, e.g., polymerase chain reaction. Allelic variants of these sequences within a species (i.e., sequences containing some individual nucleotide differences from a more commonly occurring sequence within a species, but which nevertheless encode the same protein) such as other human variants of BAP-1 SEQ ID NO: 2, may also be readily obtained given the knowledge of his sequence provided by this invention.

The present invention further encompasses nucleic acid sequences capable of hybridizing under stringent conditions [see, J. Sambrook et al, *Molecular Cloning: A Laboratory Manual*, 2d ed., Cold Spring Harbor Laboratory (1989)] to the sequences of SEQ ID NO: 1, their anti-sense strands, or biologically active fragments thereof. An example of a highly stringent hybridization condition is hybridization at 2×SSC at 65° C., followed by a washing in 0.1×SSC at 65° C. for an hour. Alternatively, an exemplary highly stringent hybridization condition is in 50% formamide, 4×SSC at 42° C. Moderately high stringency conditions may also prove useful, e.g. hybridization in 4×SSC at 55° C., followed by washing in 0.1×SSC at 37° C. for an hour. An alternative exemplary moderately high stringency hybridization condition is in 50% formamide, 4×SSC at 30° C.

Also encompassed within this invention are fragments of the above-identified nucleic acid sequences. Preferably, such fragments are characterized by encoding a biologically active portion of BAP-1, e.g., an epitope. Generally, these oligonucleotide fragments are at least 15 nucleotides in length. However, oligonucleotide fragments of varying sizes may be selected as desired. Such fragments may be used for such purposes as performing the PCR, e.g., on a biopsied tissue sample. For example, particularly useful fragments of BAP-1 cDNA [SEQ ID NO:1] and corresponding sequences include the open reading frame, nt 40–2226, the nuclear localization sites, nt 2005 to 2022 and nt 2188 to 2205, a region of acidity at nt 1225 to 1263, and the BRCA1-RF-interactive domain at nt 1831 to 2226 of SEQ ID NO:1. Other fragments which are contained within the above identified fragments or which overlap them and demonstrate similar biological activities, e.g., those which differ by 1 to 9 bases, are also desirable. Similarly, other useful fragments may be readily identified by one of skill in the art by resort to conventional techniques, such as, by deletion mutagenesis, fusion to other proteins, or by motif searches in computer databases. In addition, other suitable techniques are known.

The nucleotide sequences of the invention may be isolated by conventional uses of polymerase chain reaction or cloning techniques such as those described in obtaining the murine and human sequences, described below. Alternatively, these sequences may be constructed using conventional genetic engineering or chemical synthesis techniques.

According to the invention, the nucleic acid sequences may be modified. Utilizing the sequence data in FIGS. 3A–3E [SEQ ID NO: 1] and in the sequence listing, it is within the skill of the art to obtain other polynucleotide sequences encoding the proteins of the invention. Such modifications at the nucleic acid level include, for example, modifications to the nucleotide sequences which are silent or which change the amino acids, e.g. to improve expression or secretion. Also included are allelic variations, caused by the natural degeneracy of the genetic code.

Also encompassed by the present invention are mutants of the BAP-1 gene provided herein. Such mutants include amino terminal, carboxy terminal or internal deletions which are useful as dominant inhibitor genes. Such a truncated, or deletion, mutant may be expressed for the purpose of inhibiting the activity of the full-length or wild-type gene.

These nucleic acid sequences are useful for a variety of diagnostic and therapeutic uses. Advantageously, the nucleic acid sequences are useful in the development of diagnostic probes and antisense probes for use in the detection and diagnosis of conditions characterized by BRCA1 mutation. Additionally, the BAP-1 gene has been mapped to chromosome 3p21.3. Thus, these sequences provide a good marker for further analysis of chromosome 3. The nucleic acid sequences of this invention are also useful in the production of mammalian, and particularly, human BAP-1 proteins and peptides.

II. Protein Sequences

The present invention also provides mammalian BAP-1 polypeptides, peptides or proteins. These proteins are free from association with other contaminating proteins or materials with which they are found in nature. In one embodiment, the invention provides a human BAP-1 [SEQ ID NO:2] polypeptide of 729 amino acids having a predicted molecular weight (MW) of about 81 kD. In another embodiment, the invention provides partial human and murine BAP-1 proteins [SEQ ID NO: 6–9] (FIG. 2B).

Also included in the invention are analogs, or modified versions, of the proteins provided herein. Typically, such analogs differ by only one to four codon changes. Examples include polypeptides with minor amino acid variations from the illustrated amino acid sequences of BAP-1 (FIGS. 3A–3E) [SEQ ID NO: 2]; in particular, conservative amino acid replacements. Conservative replacements are those that take place within a family of amino acids that are related in their side chains and chemical properties. Also provided are homologs of the proteins of the invention which are characterized by having at least about 85% or higher homology with SEQ ID NO:2. Based on the sequence information provided herein, one of skill in the art can readily obtain BAP-1 from other mammalian species.

Further encompassed by this invention are fragments of the BAP-1 polypeptide. Such fragments are desirably characterized by having BAP-1 biological activity, including, e.g., the ability to bind specifically to the RING finger domain of wild-type BRCA1. These fragments may be designed or obtained in any desired length, including as small as about 5–8 amino acids in length. Such a fragment may represent an epitope of the protein. Alternatively, the BAP-1 proteins [SEQ ID NO:2] of the invention may be modified, for example, by truncation at the amino or carboxy termini, by elimination or substitution of one or more amino acids, or by any number of now conventional techniques to improve production thereof, to enhance protein stability or other characteristics, e.g. binding activity or bioavailability, or to confer some other desired property upon the protein.

Currently, desirable proteins or peptides correspond to the nuclear localization sites, residues 656 to 661 and residues 717 to 722 of SEQ ID NO:2, a region of extreme acidity, residues 396 to 408 SEQ ID NO:2, and the interactive domain, residues 598 to 729 of SEQ ID NO:2. Another suitable fragment, which has homology to ubiquitin carboxyl-terminal hydrolase, isozyme L3, is located between about amino acids 1 to about 214 of SEQ ID NO: 2. Yet another suitable fragment, corresponding to residues 483 to 576 of SEQ ID NO:2 has been used to generate antibodies. Other suitable fragments include amino acids 1 to 313, 1 to 325, 1 to 352, and 1 to 426 of SEQ ID NO: 2. Additionally, fragments which are about in the range of the above amino acid residues, e.g., which differ by 1 to 5 amino acids, are anticipated to be particularly desirable. Still other suitable BAP-1 fragments are identified in the Examples or may be readily identified and prepared by one of skill in the art using known techniques, such as deletion mutagenesis and expression.

III. Expression

A. In Vitro

To produce recombinant BAP-1 proteins of this invention, the DNA sequences of the invention are inserted into a suitable expression system. Desirably, a recombinant molecule or vector is constructed in which the polynucleotide sequence encoding BAP-1 is operably linked to a heterologous expression control sequence permitting expression of the BAP-1 protein. Numerous types of appropriate expression vectors are known in the art for mammalian (including human) protein expression, by standard molecular biology techniques. Such vectors may be selected from among conventional vector types including insects, e.g., baculovirus expression, or yeast, fungal, bacterial or viral expression systems. Other appropriate expression vectors, of which numerous types are known in the art, can also be used for this purpose.

Methods for obtaining such expression vectors are well-known. See, Sambrook et al, *Molecular Cloning. A Laboratory Manual*, 2d edition, Cold Spring Harbor Laboratory, New York (1989); Miller et al, *Genetic Engineerin*, 8:277–298 (Plenum Press 1986) and references cited therein.

Suitable host cells or cell lines for transfection by this method include mammalian cells, such as Human 293 cells, Chinese hamster ovary cells (CHO), the monkey COS-1 cell line or murine 3T3 cells derived from Swiss, Balb-c or NIH mice may be used. Another suitable mammalian cell line is the CV-1 cell line. Still other suitable mammalian host cells, as well as methods for transfection, culture, amplification, screening, production, and purification are known in the art. [See, e.g., Gething and Sambrook, *Nature*, 293:620–625 (1981), or alternatively, Kaufman et al, *Mol. Cell. Biol.*, 5(7):1750–1759 (1985) or Howley et al, U.S. Pat. No. 4,419,446].

Similarly bacterial cells are useful as host cells for the present invention. For example, the various strains of *E. coli* (e.g., HB101, MC1061, and strains used in the following examples) are well-known as host cells in the field of biotechnology. Various strains of *B. subtilis*, Pseudomonas, other bacilli and the like may also be employed in this method.

Many strains of yeast cells known to those skilled in the art are also available as host cells for expression of the polypeptides of the present invention. Other fungal cells may also be employed as expression systems.

Alternatively, insect cells such as *Spodoptera frugipedera* (Sf9) cells may be used.

Thus, the present invention provides a method for producing a recombinant BAP-1 protein which involves transfecting a host cell with at least one expression vector containing a polynucleotide of the invention under the control of a transcriptional regulatory sequence, e.g., by conventional means such as electroporation. The transfected or transformed host cell is then cultured under conditions that allow expression of the BAP-1 protein. The expressed protein may then be recovered, isolated, and optionally purified from the cell (or from the culture medium, if expressed extracellularly) by appropriate means known to one of skill in the art.

For example, the proteins may be isolated in soluble form following cell lysis, or may be extracted using known techniques, e.g., in guanidine chloride. If desired, the BAP-1 proteins of the invention may be produced as a fusion protein. For example, it may be desirable to produce BAP-1 fusion proteins, to enhance expression of the protein in a selected host cell, to improve purification, or for use in monitoring the presence of BAP-1 in tissues, cells or cell extracts. Suitable fusion partners for the BAP-1 proteins of the invention are well known to those of skill in the art and include, among others, β-galactosidase, glutathione-S-transferase, and poly-histidine.

B. In Vivo

Alternatively, where it is desired that the BAP-1 protein (whether full-length or a desirable fragment) be expressed in vivo, e.g., for gene therapy purposes, an appropriate vector for delivery may be readily selected by one of skill in the art. Exemplary gene therapy vectors are readily available from a variety of academic and commercial sources, and include, e.g., adeno-associated virus [International patent application No. PCT/US91/03440], adenovirus vectors [M. Kay et al, *Proc. Natl. Acad. Sci. USA*, 91:2353 (1994); S. Ishibashi et al, *J. Clin. Invest.*, 92:883 (1993)], or other viral vectors, e.g., various poxviruses, vaccinia, etc. Methods for insertion of a desired gene, e.g., BAP-1, and obtaining in vivo expression of the encoded protein, are well known to those of skill in the art.

IV. Antisera and Antibodies

The BAP-1 proteins of this invention are also useful as antigens for the development of anti-BAP-1 antisera and antibodies to BAP-1 or to a desired fragment of a BAP-1 protein. Specific antisera may be generated using known techniques. See, Sambrook, cited above, Chapter 18, generally, incorporated by reference and Example 5 below. Similarly, antibodies of the invention, both polyclonal and monoclonal, may be produced by conventional methods. These techniques may include the Kohler and Milstein hybridoma technique, recombinant techniques, such as described by Huse et al, *Science*, 246:1275–1281 (1988), or any other techniques known to the art.

Also encompassed within this invention are humanized and chimeric antibodies. As used herein, a humanized antibody is defined as an antibody containing murine complementary determining regions (CDRS) capable of binding to BAP-1 or a fragment thereof, and human framework regions. These CDRs are preferably derived from a murine monoclonal antibody (MAb) of the invention. As defined herein, a chimeric antibody is defined as an antibody containing the variable region light and heavy chains, including both CDR and framework regions, from a BAP-1 MAb of the invention and the constant region light and heavy chains from a human antibody. Methods of identifying suitable human framework regions and modifying a MAb of the invention to contain same to produce a humanized or chimeric antibody of the invention, are well known to those of skill in the art. See, e.g., E. Mark and Padlin, "Humanization of Monoclonal Antibodies", Chapter 4, *The Handbook of Experimental Pharmacology*, Vol. 113, The Pharmacology of Monoclonal Antibodies, Springer-Verlag (June, 1994). Other types of recombinantly-designed antibodies are also encompassed by this invention.

Further provided by the present invention are anti-idiotype antibodies (Ab2) and anti-anti-idiotype antibodies (Ab3). Ab2 are specific for the target to which anti-BAP-1 antibodies of the invention bind and Ab3 are similar to BAP-1 antibodies (Ab1) in their binding specificities and biological activities [see, e.g., M. Wettendorff et al., "Modulation of anti-tumor immunity by anti-idiotypic antibodies." In *Idiotypic Network and Diseases*, ed. by J. Cerny and J. Hiernaux J, Am. Soc. Microbiol., Washington D.C.: pp. 203–229, (1990)]. These anti-idiotype and anti-anti-idiotype antibodies may be produced using techniques well known to those of skill in the art. Such anti-idiotype antibodies (Ab2) can bear the internal image of BAP-1 and bind to BRCA1 in much the same manner as BAP-1, and are thus useful for the same purposes as BAP-1.

In general, polyclonal antisera, monoclonal antibodies and other antibodies which bind to BAP-1 as the antigen (Ab1) are useful to identify epitopes of BAP-1, to separate BAP-1 from contaminants in living tissue (e.g., in chromatographic columns and the like), and in general as research tools and as starting material essential for the development of other types of antibodies described above. Anti-idiotype antibodies (Ab2) are useful for binding BRCA1 and thus may be used in the treatment of cancers. The Ab3 antibodies may be useful for the same reason the Ab1 are useful. Other uses as research tools and as components for separation of BAP-1 from other contaminant of living tissue, for example, are also contemplated for the above-described antibodies.

V. Diagnostic Reagents and Methods

Advantageously, the present invention provides reagents and methods useful in detecting and diagnosing abnormal levels of BAP-1, (i.e., deficiencies or excesses thereof) in a patient. Conditions associated with excess levels of BAP-1 may be indicative of BRCA1 mutations. Abnormal levels of BAP-1 may be associated with a variety of cancers, including lung cancer (small cell lung carcinoma and non-small cell lung carcinoma), breast cancers, uterine carcinomas, and oral squamous cell carcinomas, among others.

Thus, the proteins, protein fragments, antibodies, and polynucleotide sequences (including anti-sense polynucleotide sequences and oligonucleotide fragments), and BAP-1 antisera and antibodies of this invention may be useful as diagnostic reagents. These reagents may optionally be labelled using diagnostic labels, such as radioactive labels, calorimetric enzyme label systems and the like conventionally used in diagnostic or therapeutic methods. Alternatively, the N- or C-terminus of BAP-1 or a fragment thereof may be tagged with a viral epitope which can be recognized by a specific antisera. The reagents may be used to measure abnormal BAP-1 levels in selected mammalian tissue using conventional diagnostic assays, e.g., Southern blotting, Northern and Western blotting, polymerase chain reaction (PCR), reverse transcriptase (RT) PCR, immunostaining, and the like. For example, in biopsies of tumor tissue, loss of BAP-1 expression in tumor tissue could be directly verified by RT-PCR or immunostaining. Alternatively, a Southern analysis, genomic PCR, or fluorescence in situ hybridization (FISH) may be performed to confirm BAP-1 gene rearrangement.

In one example, as diagnostic agents the polynucleotide sequences may be employed to detect or quantitate normal BAP-1. The selection of the appropriate assay format and label system is within the skill of the art and may readily be chosen without requiring additional explanation by resort to the wealth of art in the diagnostic area.

Thus the present invention provides methods for the detection of disorders characterized by inappropriate BAP-1 levels. The protein, antibody, antisera and polynucleotide reagents of the invention are expected to be useful in the following methods. The methods involve contacting a selected mammalian tissue, e.g., a biopsy sample or other cells, with the selected reagent, protein, antisera antibody or DNA sequence, and measuring or detecting the amount of BAP-1 present in the tissue in a selected assay format based on the binding or hybridization of the reagent to the tissue.

VI. Therapeutic Compositions and Methods

BAP-1 is believed to have a role in modulating the activity of BRCA1, a tumor suppressor. More particularly, BAP-1 enzymatic activity is anticipated to have a role in the persistence of BRCA1 in a cell. For example, the extended presence of BRCA1, particularly in high levels, is associated with cell death. Thus, by adjusting BAP-1 levels in a cell, e.g., by use of BAP-1 or an inhibitor identified by the invention, persistence of BRCA-1 in the cells can thereby be altered. For example, it may be desirable to adjust BAP-1 levels so as to enhance BRCA1 persistence in a cell, e.g., a tumor cell. Alternatively, it may be desirable to adjust BAP-1 levels so as to increase BRCA1 degradation in the cell. The compositions and methods useful for the treatment of conditions associated with inadequate or undesirable BAP-1 levels are provided. As stated above, included among such conditions are liver and breast cancers.

The therapeutic compositions of the invention may be formulated to contain an anti-idiotype antibody of the invention, the BAP-1 protein itself or a fragment thereof. The therapeutic composition desirably contains 0.01 μg to 10 mg protein. These compositions may contain a pharmaceutically acceptable carrier. Suitable carriers are well known to those of skill in the art and include, for example, saline. Alternatively, such compositions may include conventional delivery systems into which protein of the invention is incorporated. Optionally, these compositions may contain other active ingredients, e.g., chemotherapeutics.

Still another method involves the use of the BAP-1 polynucleotide sequences for gene therapy. In the method, the BAP-1 sequences are introduced into a suitable vector for delivery to a cell containing a deficiency of BAP-1 and/or to block tumor growth. By conventional genetic engineering techniques, the BAP-1 gene sequence may be introduced to mutate the existing gene by recombination or to replace an inactive or missing gene.

Generally, a suitable vector-based treatment contains between $1 \times 10^{-3}$ pfu to $1 \times 10^{-12}$ pfu per dose. However, the dose, timing and mode of administration of these compositions may be determined by one of skill in the art. Such factors as the age, condition, and the level of the BAP-1 deficiency detected by the diagnostic methods described above, may be taken into account in determining the dose, timing and mode of administration of the therapeutic compositions of the invention. Generally, where treatment of an existing cancer is indicated, a therapeutic composition of the invention is preferably administered in a site-directed manner and is repeated as needed. Such therapy may be administered in conjunction with conventional therapies, including radiation and/or chemotherapeutic treatments.

VII. Drug Screening and Development

The proteins, antibodies and polynucleotide sequences of the present invention may also be used in the screening and development of chemical compounds or proteins which have utility as therapeutic drugs for the treatment of cancers characterized by BAP-1 and/or BRCA1 mutation or loss. As one example, a compound capable of binding to BAP-1 and preventing its biological activity may be a useful drug component for the treatment or prevention of cancer. The methods described herein may also be applied to fragments of BAP-1.

Suitable assay methods may be readily determined by one of skill in the art. Where desired, and depending on the assay selected, BAP-1 may be immobilized directly or indirectly (e.g., via an anti-BAP-1 antibody) on a suitable surface, e.g., in an ELISA format. Such immobilization surfaces are well known. For example, a wettable inert bead may be used. Alternatively, BAP-1 may be used in screening assays which do not require immobilization, e.g., in the screening of combinatorial libraries.

Assays and techniques exist for the screening and development of drugs capable of binding to selected regions of BAP-1. These include the use of phage display system for expressing the BAP-1 proteins, and using a culture of transfected E. coli or other microorganism to produce the proteins for binding studies of potential binding compounds. See, for example, the techniques described in G. Cesarini, *FEBS Letters*, 307(1):66–70 (July 1992); H. Gram et al., *J. Immunol. Meth.*, 161:169–176 (1993); C. Summer et al., *Proc. Natl. Acad. Sci., USA*, 89:3756–3760 (May 1992), incorporated by reference herein.

Other conventional drug screening techniques may be employed using the proteins, antibodies or polynucleotide sequences of this invention. As one example, a method for identifying compounds which specifically bind to a BAP-1 protein can include simply the steps of contacting a selected BAP-1 protein with a test compound to permit binding of the test compound to BAP-1; and determining the amount of test compound, if any, which is bound to the BAP-1 protein. Such a method may involve the incubation of the test compound and the BAP-1 protein immobilized on a solid support.

Typically, the surface containing the immobilized ligand is permitted to come into contact with a solution containing the BAP-1 protein and binding is measured using an appropriate detection system. Suitable detection systems include the streptavidin horse radish peroxidase conjugate, direct conjugation by a tag, e.g., fluorescein. Other systems are well known to those of skill in the art. This invention is not limited by the detection system used.

Another method of identifying compounds which specifically bind to BAP-1 can include the steps of contacting a BAP-1 protein immobilized on a solid support with both a test compound and the protein sequence which is a receptor for BAP-1 to permit binding of the receptor to the BAP-1 protein; and determining the amount of the receptor which is bound to the BAP-1 protein. The inhibition of binding of the normal protein by the test compound thereby indicates binding of the test compound to the BAP-1 protein.

Thus, through use of such methods, the present invention is anticipated to provide compounds capable of interacting with BAP-1 or portions thereof, and either enhancing or decreasing its biological activity, as desired. Such compounds are believed to be encompassed by this invention.

The assay methods described herein are also useful in screening for inhibition of the interaction between a BAP-1 protein of the invention and its ligand(s). The solution containing the inhibitors may be obtained from any appropriate source, including, for example, extracts of supernatants from culture of bioorganisms, extracts from organisms collected from natural sources, chemical compounds, and mixtures thereof.

These examples illustrate the preferred methods for obtaining and using the sequences and compositions of the invention. These examples are illustrative only and do not limit the scope of the invention.

EXAMPLE 1
Construction of Expression Plasmids

A. LexA Fusions

A totally synthetic BRCA1 gene encoding the amino-terminal 100 amino acids of human BRCA1 (BRCA1-RF), including the full ring-finger domain, was constructed. The BRCA1-RF domain was made using long overlapping oligonucleotides and PCR-mediated overlap-extension gene synthesis techniques [Madden et al, *Science*, 253:1550–1553 (1991)]. Codon usage was optimized for expression in *E. coli* and *S. cerevisiae* [Sharp et al, *Nuc. Acids Res.*, 16:8207–8211 (1988)] (FIGS. 1A and 1B). The following oligonucleotides were used.

top strand: [SEQ ID NO: 10]
5'-ATGGAACCTGTCTGCTCTGCGTGTTGAA
AAGTTCAAAACGTTATCAACGCTATG-
CAAAAGATCCTGGAATGTCCAATCTG bottom strand: [SEQ ID NO: 11]
5'-GGTTCAGCAGCTTCAGCATACAGAACTT
ACAGAAGATGTGGTCACACTTAGTG-
GAAACTGGTTCCTTGATCAGTTCCAGA-
CAGATTGGACATTCCAGGATC top strand: [SEQ ID NO: 12]
5'-GTATGCTGAAGCTGCTGAACCAAAAGAA
GGGTCCATCTCAATGTCCACTGTGTAA-
GAACGACATCACTAAGCGTTCTCTGCAA-
GAATCTACTCGTTTCTCTC bottom strand: [SEQ ID NO: 13]
5'-TTCCAGACCAGTGTCCAGCTGGAAAGC
ACAGATGATCTTCAGCAGTTCTTCAAC-
CAGTTGAGAGAAACGAGTAGATTCTTG Double-stranded DNA was generated by 5 cycles of the polymerase chain reaction (PCR) and the full-length cDNA was amplified further via PCR using "outside" primers with homology to the 5' and 3' ends of the DNA sequence [Madden, cited above]. These primers contained enzymatic restriction sites for either EcoRI (BRCA1-RF-5' primer): 5'-GCTAGAATTCACCATGGACCTGTCTCCTCTG [SEQ ID NO: 14] or Sal I (BRCA1-RF-3' primer): 5'-GCTAGTCGACTTCCAGACCAGTGTCCAG [SEQ ID NO: 15].

The resulting complete, "wild-type" RF domain was confirmed by sequencing. The resulting BRCA1-RF was then fused in frame with the LexA DNA-binding domain to create a LexA-BRCA1-RF fusion construct by cloning the BRCA1-RF domain into the EcoRI-SalI restriction sites of the vector pBTM-116 [Vojtek et al, *Cell*, 74:205–214 (1993)] (see FIG. 1B). This LexA-BRCA1-RF construct was used as the probe ("bait") to screen for BRCA1-interacting proteins in a yeast 2-hybrid analysis.

Negative control/specificity controls for the specificity of the interaction in the yeast system were made (as LexA fusions) by mutating the BRCA1-RF (FIGS. 1A and 1B) as follows:

(i) The Cys61Gly and Cys64Gly substitutions of BRCA1 which occur in breast cancer pedigrees. BRCA1 RF domain point mutants, BRCA1-C64G (Cys 64 to Gly) and BRCA1-C61 G (Cys 61 to Gly), were created by PCR-mutagenesis using the "outside" primers described above and overlapping oligonucleotides containing the appropriate nucleotide change: BRCA1-C61 G-sense: 5'-CCATCTCAAGGTCCACTGTGTAAG-3' [SEQ ID NO: 25]; BRCA1-C61 G-antisense: 5'CTTACACAGTGGACCTTGAGATGG-3' [SEQ ID NO: 26]; BRCA1-C64G-sense: 5'-CAATGTCCACTGGGTAAGAACGACATC-3' [SEQ ID NO: 27]; and BRCA1-C64G-antisense: 5'-GATGTCGTTCTTACCCAGTGGACATTG-3' [SEQ ID NO: 28] [Ho et al, *Gene*, 77:51–59 (1989)]. The BRCA1 (C64G)-RF control has a point mutation in the BRCA1-RF found in a breast cancer kindred [Castilla et al, *Nat. Genet.*, 8:387–391 (1994)]. This mutation, a Cys64 to Gly64, destroys one of the Zn chelating residues leading, presumably, to the loss of correct conformation of the RING domain.

(ii) The protein equivalent of the del AG185 mutation which results in a frame shift at amino acid 22 followed by 17 out-of-frame amino acids and a stop codon. The BRCA1-delAG185 mutant was generated by PCR using the BRCA1-RF-5' oligonucleotide [SEQ ID NO: 14] and a 3' oligonucleotide that encoded the changed amino acid sequence: 5'-GCATGGATCCTCAAACCTTGTGCAGGCAGG TACCCTGGTCAACAGGAGACAGGTGGGAAACC AGGATCTTTTGCATAGC-3' [SEQ ID NO: 29]. The truncated protein generated by the delAG185 mutation is found in high frequency in the Ashkenazi population [Struewing et al, *Nat. Genet.*, 11:198–200 (1995)].

(iii) A truncated BRCA1 RING finger at amino acid 31, the result of a PCR error. The BRCA1-del31 truncation mutant was a mis-primed PCR reaction of BRCA1-RF identified by sequencing during the initial screens for a wild-type LexA-BRCA1. The BRCA1-RF-trunc control is a truncation of the BRCA1-RF, a protein of 35 amino acids which ends within the first loop of the RING domain.

(iv) The RPT-1 RING finger domain. The LexA-RPT-1 construct (amino acids 1–100) [SEQ ID NO: 5] was made by PCR-mediated amplification of the nucleotides representing the first 100 amino acids of the transcription factor RPT-1 [Patarca et al, *Proc. Natl. Acad. Sci. USA*, 85:2733–2737 (1988); RPT-1 cDNA kindly provided by Dr. H. Cantor] with the 5' and 3' primers incorporating EcoRI and Sal I restriction sites.

(v) A non-specific control LexA fusion with RhoB. LexA-RhoB was a kind gift of Dr. George Prendergast, The Wistar Institute of Anatomy and Biology, Philadelphia, Pa.

All LexA mutant fusion constructs were made, as described for the wild-type BRCA1-RF, by cloning the appropriate mutated BRCA1-RF domain into the vector pBTM-116. The RPT-1 PCR product was enzymatically digested and ligated into the corresponding sites in pBTM-116. All clones were confirmed by sequencing.

The wild-type BRCA1-RF did not display intrinsic transcriptional activation function in yeast and proper expression of each LexA fusion in yeast was confirmed by Western blot analysis with anti-LexA DNA-binding domain antibody (data not shown).

These controls screen for proteins which interact only with wild-type the BRCA1-RF and not with any of the physiologically relevant BRCA1-RF mutations nor a RING finger that is the most similar to that of the BRCA1-RF [Miki et al, *Science*, 266:66–71 (1994)]. Thus, the controls make it possible to identify proteins which interact specifically with the BRCA1-RF and not with any other RING domain.

EXAMPLE 2

Yeast Two-Hybrid Screen for BRCA1-RF Interacting Proteins

To identify the potential protein partners of BRCA1, a yeast 2-hybrid analysis system as modified by Stan Hollenberg [Vojtek et al, cited above] was performed using the RING finger domain of human BRCA1. Guided by the expression patterns of BRCA1 during mouse development and in human spleen, the cDNA libraries selected for screening with the LexA-BRCA1-RF of Example 1 were (1) the human adult B cell, oligo-dT-primed, cDNA library [Durfee et al, *Genes & Devel.*, 7:555–569 (1993) (a kind gift of Dr. Steve Elledge)] and (2) a whole mouse embryo (9.5–10.5 day), random-primed, cDNA library size selected for inserts of 300 to 500 base pairs in length [Vojtek et al, cited above; kind gift of Dr. Stan Hollenberg)].

Briefly, the LexA-BRCA1-RF and a selected library were co-transformed into the L40 yeast strain. Positive protein interactions were selected by His auxotrophy. Fifty colonies were picked and grown for 10 generations without selection for the LexA-BRCA1-RF plasmid. Isolated clones of each colony, which were positive for the presence of only the library plasmid, were picked and mated with AMR70 yeast containing LexA-BRCA1-RF, one of its mutants, or one of the LexA controls of Example 1A. Positive matings were selected by growth on media requiring the presence of both plasmids. These colonies were then scored for LacZ production (positive interaction) and those which were positive for interaction with the wild-type BRCA1-RF, but not any of the controls, were processed for further analysis.

Using the above assay methods, one hundred yeast colonies (50 from each library; each screen representing approximately $8-10 \times 10^6$ independent cDNAs), randomly taken from approximately 5–700 total colonies which grew on solid media lacking the amino acid histidine, were selected for additional screening.

Thirty-one cDNAs which specifically interacted with BRCA1-RF were obtained from the secondary screen of the two libraries. Eight of these (3 from the human library and 5 from the mouse library) encoded the same amino acid sequences.

A representative secondary screen of one of the human clones, hBAP-1 (aa483–729; SEQ ID NO: 6), and 3 of the mouse clones, mBAP-1 (aa581–720; SEQ ID NO: 8), mBAP-1 (aa518-{del}-718; SEQ ID NO: 7), and mBAP-1 (aa596–721; SEQ ID NO: 9) was performed by re-introducing the purified pACT plasmids containing them into naive yeast. The sequences of these clones are compared in FIG. 2B. This screen showed that each clone showed a strong interaction with the wild-type BRCA1 ring-finger, but failed to interact with the C64G, C61G, del31, delAG, RPT-1, RhoB, or any of the specificity control LexA fusions (data not shown).

Thus, these clones specifically interact with only the BRCA1 RING finger. These cDNA clones all encode the same region of the same protein which has been termed BRCA1-Associated Protein-1 or BAP-1. Each clone shares the same translational reading frame with the transcriptional activation domain to which it is fused. In addition, the fusion junctions were different among the clones suggesting that the interaction was not due to a fusion-junction artifact.

The longest cDNA retrieved in the two-hybrid screen was a 2.0 kb clone from the human library and encoded 246 amino acids followed by a 1.3 kb 3'UTR. Each mouse clone encoded an overlapping, smaller subset of this human open reading frame and which served to partially map the minimal interaction domain. Further definition of this minimal interaction domain was performed by mutagenesis of this region of BAP1.

The "minimal interaction domain" was determined by the shortest mouse clone [mBAP-1 (aa596–721; SEQ ID NO: 9)]. To further define the specificity of interaction between BRCA1 and BAP-1, carboxy- and amino-terminal truncation mutants of mBAP-1 were generated by PCR-based deletion or point mutagenesis.

The appropriate region of mBAP1(596–721) was amplified by PCR using a vector primer pVP16 5'-primer, 5'-CCGATGCCCTTGGAATTGACGAG-3'; pVP16 3'-primer, 5'-CGATGAATTCGAGCTAGCTTCTATC-3' ) and the appropriate truncating oligonucleotide Mc43Ct1, 5'-GCATGAATTCTCAGCT CCGGCGCACTGAGATG-3'; Mc43Ct2, 5'-GCATGAATTCTCAAGCCAGCATGGATATGAAGG-3'; Mc43Ct3, 5'-GCATGAATTCTCAGTCATCAATCTTGAACTTC-3'; Mc43Ct4, 5'-GCATGAATTCTCATGCAATCTCGGCTTCTAC-3'; or Mc43Nt1, 5'-GCATG GATCCCCAAGATTGATGACCAGCGAAGG-3' [SEQ ID NOS: 30 to 36, respectively).

These oligonucleotides were generated with an incorporated EcoRI restriction site (for the 3' end oligos) or a BamHI restriction site (for the 5' end oligos). After PCR amplification, the product was cut with BamHI and EcoRI, and then ligated into the mouse library-yeast expression vector, pVP16 [Vojtek et al, cited above].

The point mutant mBAP-1 (L691P) was made by standard PCR-based mutagenesis protocols [Ho et al, Gene, 77:51–59 (1989)], using (Mc43(L691 P) sense-primer, 5'-GCTGGCCAACCCGGTGGAACAG-3' [SEQ ID NO: 37]; Mc43(L691P) antisense-primer, 5'-CTGTTCCACCGGGTTGGCCAGC-3' [SEQ ID NO: 38] and using the same vector primers described above.

The "minimal interaction domain" was deleted from the human sequence (the longest clone) and this protein (hBAP-1(483–594) [SEQ ID NO: 6] was also assayed for interaction with the BRCA1-RF in the yeast 2-hybrid system.

All clones were confirmed by sequencing and expression in yeast was confirmed by western analysis using antibodies against the VP16 activation domain (data not shown). Each individual mutant was co-transformed with LexA-BRCA1-RF into L40 yeast and tested for interaction via its ability to activate transcription from the LacZ locus.

The mutants showed that deletion of protein sequence from the carboxy or amino termini of mBAP-1 (aa 596–721; SEQ ID NO: 9) almost completely destroyed the BAP1-BRCA1 interaction, suggesting a complex interface between the proteins. Deletion of the last 20 amino acids of mBAP-1 led to a significant reduction in the intensity of interaction. Further deletions from the COOH-terminus led to the complete loss of interaction between BRCA1-RF and BAP-1. A single amino-terminal truncation which deleted approximately half of mBAP-1 (aa 596–721; SEQ ID NO: 9) led to an almost complete loss of interaction. Interestingly, the mBAP(518del718) clone interacted most poorly with BRCA1-RF and lacked a 93 bp sequence (the reading frame was maintained), possibly the result of a naturally occurring splice variant. That these clones also fail to bind multiple, independent tumor-derived mutations of the BRCA1-RF provides strong genetic evidence for their relevance to the functions of BRCA1.

The results of the above experiments suggested that some critical domain was being disrupted by these truncations. A careful analysis showed that the region from amino acids 632 to 729 of SEQ ID NO: 6 may in fact generate a coiled-coil domain. A point mutation in the middle of the domain (leucine 691 substituted with a proline) destroys interaction with the BRCA1 RING structure. This result is consistent with the BAP-1/BRCA-1 interaction domain being a coiled-coil.

EXAMPLE 3

Analysis of BAP-1 cDNA

A nearly full-length cDNA was constructed via a combination of cDNA library screening, EST database searching, 5'RACE and RT-PCR (FIGS. 3A–3E) as follows. Searches of the protein and DNA databases [Altschul et al, *J. Mol. Biol.*, 215:403–410 (1990)] with the BAP-1 protein/cDNA sequences obtained from the screening of Example 2, showed no significant matches with any known protein or cDNA. However, searches of the EST databases with BAP-1 cDNA yielded several "hits", including one whose clone had a 5' sequence that overlapped with the 3' sequence of another EST clone. The clones defined by these EST's were obtained from the I.M.A.G.E. consortium [Lennon et al, *Genomics*, 33:151–152 (1996); clones #46154 and #40642]. A partial BAP-1 cDNA clone (EST-BAP1) was generated by digesting clone #40642 with Hind III and Fsp I and clone #46154 with Fsp I and EcoRI. These two pieces were then ligated into the Hind III and EcoRI sites of the vector pcDNA3 (Invitrogen).

Analysis of the IMAGE consortium cDNA and its open-reading-frames suggested that this BAP-1 cDNA, as constructed, was not complete. Reverse-transcriptase-PCR was performed on RNA from normal human fibroblasts using a gene-specific primer: 5'-GAAGCGGATGTCGTGGTAGG-3' [SEQ ID NO: 43] and identified 62 nucleotides which were missing from the "EST-BAP1" cDNA. These 62 nucleotides were inserted into the "EST-BAP1" cDNA by digestion of the RT-PCR product with the restriction enzymes KpnI, which is a unique site within the 5' RT-PCR oligonucleotide: 5'CCTGTTAT-TAACCCTCACTAAAGGGAAGGGTA CCATGAATAAGGGCTGGCTGGAGC-3' [SEQ ID NO: 39] and 3' RT-PCR-oligonucleotide: 5'-GAAGCGGATGTCGTGGTAGG-3' [SEQ ID NO: 40, and AvrII. Ligation of the KpnI/AvrII digested RT-PCR fragment and AvrII/EcoRI digested "EST-BAP1" cDNA and the KpnI-EcoRI digested pcDNA3, produced the full-length BAP-1 cDNA.

Thus, BAP1 cDNA (FIGS. 3A to 3E; SEQ ID NO: 1] comprises 3525 bp, including a polyA tract with multiple polyA signals. Conceptual translation yields a long open reading frame of 729 amino acids [SEQ ID NO: 2] with a predicted MW of about 81 kDa and pI of 6.3.

The presumptive initiator methionine is within a favorable context for translation start, however the short 5'UTR of 39 bp encodes amino acids in-frame with the presumptive methionine and does not contain a stop codon. BLAST searches and a domain analysis [Henikoff & Henikoff, *Genomics*, 19:97–107 (1994)] indicated that BAP1 is a novel protein with motifs suggestive of function.

The amino-terminal 1–240 amino acids of SEQ ID NO: 2 show significant homology to a class of thiol proteases, designated ubiquitin C-terminal hydrolase (UCH), particularly Isozyme L3, which are implicated in the proteolytic processing of ubiquitin [Wilkinson et al, *Science*, 246:670–673 (1989)]. These enzymes play a key role in protein degradation via the ubiquitin-dependent proteasome pathway. The most closely related UCH is a hypothesized protein from *C. elegans* UCH-CAEEL, which shares 63% similarity (40% identity) with BAP1 through the UCH domain and is also likely to be a UCH enzyme. Pairwise similarities to other mammalian UCHs of 54% (UCHL3) and 56% (UCHL1) have also been found. Most importantly, the residues which form the catalytic site of BAP1 (Q85, C91, H169, and D184 of FIGS. 3A–3E; SEQ ID NO: 2) are completely conserved, including the FELDG motif [Larsen et al, *Biochemistry*, 35:6735–6744 (1996)]. In addition, a loop of highly variable sequence, which is disordered in the crystallographic structure of human UCH-L3 [Johnston et al, *EMBO J.*, 16:3787–3796 (1997)], is present (residues 140 to 167 of SEQ ID NO. 2). This loop may occlude the active site or provide substrate specificity for the enzyme.

BAP1 has a number of additional motifs; a region of extreme acidity spanning amino acids 396 to 408 of SEQ ID NO. 2, as well as multiple potential phosphorylation sites and N-linked glycosylation sites. The C-terminal one-third is highly charged and is rich in proline, serine and threonine. The extreme C-terminus contains two putative nuclear localization signals, KRKKFK and RRKRSR (aa 656–661 and aa 717–722 of SEQ ID NO: 2), and is hydrophilic; it is predicted to fold into a helical (possibly coiled-coil) structure. Indeed, within the BAP1 minimal interaction domain, (i.e., from about amino acid 596 to 729 of SEQ ID NO: 2) the mutation of leucine 691 to a proline, a change predicted to disrupt the helical nature of this region, abolished the BAP1-BRCA1 interaction, consistent with the hypothesis that BAP1 uses a coiled-coil domain to interact with the RING finger domain of BRCA1. This overall architecture suggests that BAP1 is a new, structurally complex, and nuclear localized member of the UCH enzyme family.

EXAMPLE 4

In Vitro Protein Association

The direct interaction of the BRCA1-RF with BAP-1 was confirmed by binding of the BRCA1-RF to the fusion proteins of glutathione-S-transferase with BAP1.

A. The BAP/GST Constructs

The original B cell library two-hybrid BAP-1 clone obtained from the screening experiments described in Example 2 was pACT-hBAP1(483–729), which contained BAP1 amino acids 483–729 (nucleotides 1486 to 3525) [SEQ ID NOs: 2 and 1, respectively)] in the pACT plasmid backbone. The glutathione S-transferase/BAP1 fusion protein, GST-hBAP1(483–729 of SEQ ID NO: 2), was generated by cloning nucleotides 1486 to 3525 of SEQ ID NO: 1 from that original clone into pGEX-5x-1 (Pharmacia Biotech, Inc.).

Another BAP1 construct which lacked the minimal BRCA1 interaction domain pACT-hBAP1(483–594 of SEQ ID NO: 2), was generated and amplified by PCR using a pACT 5' vector primer 5'-GATGTATATAACTATCTATTCG-3' [SEQ ID NO: 41] and the BAP 1-trunc. oligonucleotide: 5'-GCATAGATCTTCACCCCTGGCTGCCTTGGATTGG3' [SEQ ID NO: 42], which amplifies BAP1 nucleotides 1486–1821 of SEQ ID NO: 1. The resulting sequence was digested with restriction enzymes and ligated into the vector pACT. Another fusion protein GST-hBAP1(483–594 of SEQ ID NO: 2) lacking the minimal BAP1 interaction domain, was generated in the same manner as pACT-hBAP1 (483–594 of SEQ ID NO: 2), described above, but fused to GST, and the BAP1 fusion constructs GST-hBAP1 (483–729 of SEQ ID NO: 2) and GST-hBAP1(483–594 of SEQ ID NO: 2), were expressed in *E. coli* and then purified [Frangioni et al, *Anal. Biochem.*, 210:179–187 (1993)]. $^{35}$S-LexA-BRCA1-RF and $^{35}$S-BRCA1 were produced in vitro via coupled transcription/translation (TNT®, Promega Corp., Madison, Wis.) in the presence of $^{35}$S-Met.

B. Association Assay

Association between the proteins was assayed essentially as described by Barlev et al, *J. Biol. Chem.*, 270:19337–19344 (1995). Briefly, each GST resin was incubated with the LexA-BRCA1-RF in 100 μL of incubation buffer (PBS containing 0.2 mM ZnSO$_4$, 0.05% NP-40 and 1 mM PMSF) for 1 hour at 4° C. followed by a second hour at room temperature. The resin and associated proteins were then washed in incubation buffer twice (1 mL at room temperature for 15 minutes) followed by four washes in PBS containing 300 mM NaCl, 0.2 mM ZnSO$_4$, 0.1% NP-40 and 1 mM PMSF. The associated proteins which remained bound to resin were eluted from the resin two times (15 minutes), each with 250 μL of elution buffer (100 mM TRIS, pH 8.0, 150 mM NaCl, 0.1% NP-40, 20 mM reduced glutathione). The two elutions were combined, concentrated to a volume of approximately 20 μL of a 50:50 resin slurry, and analyzed by SDS-PAGE and visualized by Coomassie blue staining and fluorography.

Association of the BRCA1-RF with BAP1 was confirmed in vitro by specific binding of $^{35}$S-labeled LexA-BRCA1-RF to GST-hBAP1(483–729 of SEQ ID NO: 2) fusion protein, but not to GST alone, confirming a physical association of the two proteins.

To confirm that the association of the BRCA1-RF to BAP1 was not an artifact of using only a portion of BRCA1, full length BRCA1 was expressed in vitro and incubated with GST and GST-hBAP1(483–729 of SEQ ID NO: 2). As a further control for the specificity of the interaction, BRCA1 was also incubated with GST-hBAP1(483–594 of SEQ ID NO: 2), the GST-BAP1 fusion protein lacking the minimal interaction domain.

The BRCA1 protein specifically bound to GST-hBAP1 (483–729 of SEQ ID NO: 2) and not to GST or GST-hBAP1 (483–594 of SEQ ID NO: 2), confirming the direct interaction of BRCA1 with BAP1 through the C-terminal region of BAP1.

EXAMPLE 5

Generation of Antibodies

Oligonucleotide primers (pACT 5'-vector primer 5'-GATGTATATAACTATCTATTCG-3' [SEQ ID NO: 44'; BAP1 3' primer (antibody) 5-CGTAGTCGACTGTCAGCGCCAGGGGACTC-3' [SEQ ID NO: 45]), were used to amplify the portion of the BAP1 cDNA [SEQ ID NO: 1] corresponding to amino acids 483 to 576 of SEQ ID NO: 2 via PCR cloning. The PCR product was then digested with the appropriate restriction enzymes and ligated to the COOH-terminus of 6 Histidine residues of the vector pQE-30 (QIAGEN Inc.).

The His-tagged protein was purified from *E. coli* over a Ni-agarose column as described [Friedman et al, cited above] and was used to immunize rabbits for the production of polyclonal antibodies (Cocalico Biologicals, Inc.).

EXAMPLE 6

Protein Expression of BAP1

COS-1 cells were grown at 37° C., 5% CO2 in DMEM supplemented with 10% fetal bovine serum and 2 mM L-glutamine. COS1 cells were transiently transfected using DOSPOR transfection reagent (Boehringer Mannheim Biochemicals) following the manufacturers protocol with plasmids containing the BAP1 cDNA, e.g., pACT-hBAP1 (483–729 of SEQ ID NO: 2). The BAP1 cDNA was transcribed and translated in vitro in the presence of $^{35}$S-Methionine. $^{35}$S-labeled cytosolic and nuclear extracts were then prepared from transiently transfected COS1 cells.

Immunoprecipitation of BAP1 was performed by previously described procedures for the metabolic labeling and immunoprecipitation of proteins from cell lysates [Morris et al, Oncogene, 6:2339–2348, (1991); Rauscher et al, Science, 240:1010–1016 (1988); Friedman et al, cited above] with either pre-immune or anti-BAP1 seras described in the above example.

As a control for nuclear localization, KAP-1, a co-repressor of transcription localized to the nucleus (Friedman et al, Genes Dev., 10:2067–2078, (1996)], was also immunoprecipitated from these cell fractions. Immunoprecipitation of this product with anti-BAP-1 antiserum confirmed that the protein expressed in vitro from the cDNA resulted in a polypeptide that contained the antigen used to raise the antibodies produced as described above. BAP-1 was found primarily in the nuclear fraction although a significant amount was detected in the cytosol. However, this may be an artifact of the cell fractionation procedure, since KAP-1 was also found to be present in both cytosolic and nuclear fractions and in approximately the same ratio as BAP-1.

The expression of the BAP-1 cDNA in COS1 cells in vitro followed by immunoprecipitation of $^{35}$S-labeled whole cell extract and analysis by SDS-PAGE also yielded a single major protein with an apparent molecular weight of about 91 kDa. However, the largest BAP1 open reading frame encodes a protein of about 81 kDa predicted molecular weight. The difference between apparent and predicted molecular weights may be accounted for by unusual properties of the C-terminus or by post-translational modifications.

EXAMPLE 7

Tissue and Cellular Expression of BAP-1

A. BAP1 is Expressed in a Variety of Tissues

The direct interaction between BAP1 and BRCA1 illustrated in Example 4, suggests that BAP1 might be expressed in an overlapping subset of tissues expressing BRCA1 and that the subcellular location of BAP1 and BRCA1 may be the same.

The expression of BAP1 in a variety of human adult tissues was determined by Northern blot analysis. Northern blot hybridizations were performed as follows: Ten μg total RNA from multiple tissue RNA blots (Clontech Laboratories, Inc., Palo Alto, Calif.), was electrophoretically gel-fractionated and transferred to Hybond N+ membranes (Amersham). The tissues represented were heart, brain, placenta, lung, liver, skeletal muscle, kidney, pancreas, spleen, thymus, prostate, testis, ovary, small intestine, colon and peripheral blood lymphocytes.

The protocols for hybridization of cDNA probes to RNA were performed as described (Clontech Laboratories, publication PR48380). Blots were hybridized with a 2.0 kbp $^{32}$P-1abeled hBAP1 cDNA (aa483–729; nucleotides 1486 to 3525) followed by washes under standard conditions and detection by autoradiography. Blots were also subsequently probed with a muscle actin cDNA.

The results indicated that the mRNA encoding BAP1 was present as a single mRNA species of about 4 kb in all tissues except testis, where a second, about 4.8 kb mRNA, was also detected. Highest expression was detected in testis, placenta and pancreas with varying levels detected in the remaining tissues. Expression of BAP1 in normal breast tissue was confirmed by RT-PCR of total RNA isolated from normal human mammary epithelial cells (HUMEC; data not shown). The level and pattern of tissue expression shown by BAP1 is similar to that shown by BRCA1 [Miki et al, cited above].

Northern blot analysis was also performed on several tumor cell lines representing a variety of tissue types. The cell line RNA blot was prepared by standard methods (Sambrook et al, cited above) with 20 μg of total RNA. Equivalent loading of RNA was confirmed by ethidium bromide staining. Hybridization of cDNA probes to RNA were performed using the Clontech protocols. This hybridization also showed a single mRNA species. The colon cell lines HT29 [ATCC HTB 28] and SK-Co-1 [ATCC HTB 39] showed no BAP-1 mRNA, suggesting some defect in the BAP-1 gene in these particular cell lines since colon tissue shows good expression of BAP-1.

B. BAP1 is a Nuclear Protein

The location of BAP1 as a nuclear protein within the cell was determined by immunofluorescence microscopy performed as previously described [Ishov et al, J. Cell Biology, 134:815–826 (1996)]. HEP2 epithelial cells were grown at 37° C., 5% $CO_2$ in DMEM supplemented with 10% fetal bovine serum (FBS) and 2 mM L-glutamine, and cells were transfected using DOSPOR transfection reagent (Boehringer Mannheim Biochemicals) following the manufacturers protocol via electroporation with the pcDNA3 vector (Invitrogen, Inc.) carrying the BAP1 cDNA.

Transfectants were analyzed by immunofluorescence staining with anti-BAP1 polyclonal antibodies, which in turn, were detected with FITC using biotin-avidin enhancement. Cells were stained for DNA with bis-benzimide (Hoechst 33258, Sigma Chemical Co.) and mounted using Fluoromount G (Fisher Scientific). Analysis was performed with a confocal scanning microscope (Leica, Inc.).

Detection of BAP1 by confocal microscopy located BAP1 almost exclusively in the nucleus of the cell consistent with its association with BRCA1, and the presence of two nuclear localization signals in the BAP1 protein sequence.

C. BAP1 is Located on Chromosome 3p21.3 and is Mutated in Non-Small Cell Lung Carcinoma.

To determine whether BAP1 was located at a chromosomal region routinely mutated in breast cancer and thus may be a tumor suppressor gene, the deletion of which plays a critical role in tumor pathogenesis, full-length BAP-1 cDNA was used in fluorescent in situ hybridization (FISH) of partial metaphases. FISH was performed as described previously [Tommerup and Vissing, Genomics, 27:259–264 (1995)] using a biotin-labelled 3.5 kb cDNA (full-length) clone of BAP-1, with corresponding DAPI-stained chromosome banding. Localization of BAP1 was based on the DAPI-band pattern and measurement of the relative distance from the short arm telomere to the signals (FLpter value).

BAP1 maps to chromosome 3p21.3. Specific signals were observed only on the midportion of the short arm of chromosome 3 with 42 of 69 analyzed metaphase spreads showing at least one specific signal. The FLpter value was 0.27+0.02, corresponding to a localization for BAP1 at 3p21.2–p21.31. This location is a region of LOH for breast cancer as well as a region frequently deleted in lung carcinomas [Buchhagen et al, Int. J. Cancer, 57:473–479 (1994); Thiberville et al, Int. J. Cancer, 64:371–377 (1995)].

EXAMPLE 8

Mutational Analysis of BAP1

The chromosomal location of BAP1 suggested the possibility of mutations within BAP1 in lung and breast tumors.

Thus, a variety of tumor cell lines were screened for mutations within the BAP1 gene by Southern, Northern and PCR-based SSCP analyses.

A. RNA/DNA Preparation

Genomic DNA from a panel of small cell lung cancer (SCLC), non-small cell lung cancer (NSCLC), breast cancer, and lymphoblastoid cell lines was prepared using standard methods. All cell lines were identified by their NCI number [Phelps et al, *J. Cell. Biochem. Suppl.*, 24:32–91 (1996)]: H727, H1466, H226, H526, H841, H1045, H289, BL1672, BL1770, H289, H847, H920, H1450, H1573, H1155, H1299, H1693. Total RNA was extracted by the cesium chloride ultracentrifugation method [Ausubel et al, *Current Protocols in Molecular Biology*, J. Kaaren ed., John Wiley & Sons, Inc. (1987)]. First strand cDNAs were synthesized from RNA by M-MLV reverse transcriptase (Gibco BRL) according to the manufacturer's instructions.

B. Single Strand Conformational Polymorphism (SSCP) Analysis

Seventeen overlapping PCR primer pairs, each with a predicted product size of approximately 200 base pairs, were designed to span the 2.2 kb open reading frame of the BAP1 cDNA sequence. cDNA (from RNA) was amplified in 20 μl PCR reactions containing 20 mM Tris HCl (pH 8.3), 50 mM KCl, 1.5 mM MgCl, 0.2 mM each dNTP, 0.1 mM each forward and reverse primer, 0.05 ml 32P-α dCTP, and 0.5 units Taq DNA Polymerase (BRL). PCR reactions were carried out in a Perkin-Elmer 9600 Thermocycler using a touchdown technique: a 2.5 minute initial denaturation at 94° C. was followed by 35 cycles of denaturation at 94° C.×30s, annealing, initially at 65° C. decreasing by 1° C. for each of the first ten cycles to 55° C.,×30s, and extension at 72° C.×30s with a final extension of 5 minutes at 72° C. PCR products were then diluted 1:10 with SSCP dye (95% formamide, 20 mM EDTA, and 0.05% each of bromophenol blue and xylene cyanol), heat denatured, and electrophoresed on 0.5×MDE gels +/− 10% glycerol. Abnormal single stranded DNA detected as autoradiographic shifts were reamplified by PCR and subjected to automated dye-terminator sequencing (ABI 373).

SSCP analysis showed a homozygous shift in H1466 detected by RT-PCR amplification spanning nts 1089 to 1286 (primers: sense 5'-CAACCCCACTCCCATTGTC-3" [SEQ ID NO: 46]; antisense 5'-GAGTTGGTGTTCTGCACGTC-3" [SEQ ID NO: 47]). Automated sequencing revealed a homozygous 8 base pair frameshift deletion in the NCI-H1466 cDNA, predicted to encode a truncated 393 amino acid BAP1 protein. This homozygous deletion was confirmed to be present in genomic DNA from the same cell line. In the NCI-H226 line, only the 2.4 kb band and an aberrant 2.6 kb band were detected.

B. Northern Analysis

These cell lines were subjected to Northern blot analysis and EcoRI digestion and then hybridized to a full-length BAP1 cDNA probe. A single 23 kb band was detected in the lymphoblastoid and most tumor cell lines (data not shown). One NSCLC line, NCI-H226, did not show the 23 kb band but did show an aberrant 30 kb band (data not shown).

Further mutational analysis was performed by screening a panel of lung cancer and lymphoblastoid cell lines for expression of BAP1 mRNA. Northern blot hybridization showed that most cell lines expressed a single 4 kb mRNA. A fainter (5.0 kb) band was visible corresponding to cross-hybridization with the 28S ribosomal component. However, two cell lines, NCI-H226 and the non-small cell lung cancer NCI-H1466 (both NSCLCs), showed undetectable levels of BAP1 expression, suggesting that BAP1 may play a critical role in NSCLC pathogenesis.

C. Southern Analysis

To further characterize this potential genomic rearrangement, genomic DNA from NCI-H226 and a smaller number of lung cancer and lymphoblastoid lines were subjected to Southern blot hybridization. Briefly, five μg of genomic DNA was subjected to restriction enzyme digestion with BamHI. Using the full-length BAP1 cDNA probe, four distinct bands at 7.5 kb, 4.0 kb, 3.0 kb, and 2.4 kb were detected which were present in all cell lines tested with the exception of NCI-H226. The non-small cell lung cancer NCI-H226 line shows an absence of the 7.5 kb, 4.0 kb, and 3.0 kb bands. An aberrant 2.6 kb band is detected in the NCI-H226 cell line.

These data clearly show that genetic alterations, including intragenic homozygous deletions, occur in BAP1.

EXAMPLE 9

BAP1 Augments the Growth Suppressive Activity of BRCA1

To determine whether BAP1 may affect cell growth itself or may affect BRCA1-mediated changes in cell growth, BRCA1 and BAP1 cDNAs were co-transfected into MCF7 breast cancer cells. This cell line was chosen for several reasons. It has been previously shown that these cells are inhibited by the overexpression of BRCA1 [Holt et al, cited above]. Both northern and RT/PCR analyses showed that BAP1 was expressed in this cell line (data not shown); and analysis of the open reading frame from BAP1 cDNA prepared from this cell line showed no mutations (data not shown).

MCF7 cells grown at 37° C., 5% CO2 in DMEM supplemented with 10% FBS and non-essential amino acids, were transfected with the following plasmid pairs: (a) empty plasmids pcDNA3 and pCMV5; (b) pcDNA3 and pCMV5-BAP1; (c) pcDNA3 and pCMV5-BAP1(165–729 of SEQ ID NO: 2); (d) pcDNA3-BRCA1 and pCMV5; (e) pcDNA3-BRCA1 and pCMV5-BAP1; (f) pcDNA3-BRCA1 and pCMV5-BAP1(165–729 of SEQ ID NO: 2); (g) pcDNA3-BRCA1-Δ11 and pCMV5; (h) pcDNA3-BRCA1-Δ11 and pcMV5-BAP1; and (i) pcDNA3-BRCA1-Δ11 and pCMV5-BAP1(165–729 of SEQ ID NO: 2) by a modified $CaPO_4$-DNA precipitation method [Holt et al, cited above].

MCF7 cells, at $2\times10^6$ cells/10 cm dish, were fed fresh medium approximately 3 hours prior to transfection and were then treated with the Ca-DNA precipitate for 4 hours. The cells were subjected to a brief shock with transfection buffer containing 15% glycerol. Twelve to sixteen hours later, the cells were trypsinized, counted and plated directly into complete medium containing 0.75 mg/mL G418 at $5\times10^5$ cells per 10 cm dish. Cells were fed fresh medium containing G418 every three to four days. Cells were stained for colonies approximately 21 to 28 days after transfection. The experiment was repeated 4 times with similar results.

The expression of BRCA1 alone (pcDNA3-BRCA1:pCMV5) decreased the number of colonies formed by these cells when compared to the empty vector control (pcDNA3:pCMV5), in agreement with other studies [Holt et al, cited above]. The co-expression of BRCA1 and BAP1 (pcDNA3-BRCA1:pCMV5-BAP1) significantly decreased the number of cell colonies (approximately 4 fold vs. BRCA1 alone) indicating that BAP1 enhances the growth suppressive actions of BRCA1. A mutant of BAP1, BAP1 (AA165–729), in which the enzymatic region is deleted but which still binds to BRCA1 (data not shown), also enhanced the growth suppression of BRCA1, but not to the same extent as the wildtype BAP1.

In contrast to BRCA1, the expression of BRCA1-Δ11 (BRCA1 missing the 11th exon) in MCF7 cells by itself had no effect on the growth of MCF7 cells. However, the co-expression of BRCA1-Δ11 and BAP1 significantly decreased the number of colonies, suggesting that the presence of BAP1 could functionally substitute for the missing 11th exon of BRCA1 and/or that BAP1 itself was an inhibitor of cell growth.

In support of this latter hypothesis, the expression of BAP1 in MCF7 cells did somewhat reduce the number of colonies formed (pcDNA3:pCMV5-BAP1). The expression of the enzymatic mutant, BAP1(165–729), alone or in combination with BRCA1-Δ11 yielded the same number of colonies. Thus, enzymatically active BAP1 enhances BRCA1-mediated suppression of growth.

EXAMPLE 10

BAP1 Enzymatic Assay

To determine whether BAP1 did indeed have UCH activity, the BAP1 cDNA was expressed in bacteria and this protein was assayed for the ability to hydrolyze the glycine 76 ethyl ester of ubiquitin [Ub-OEt; Mayer et al, *Biochemistry*, 28:166–172 (1989)].

Briefly, bacteria (*E. coli* DH5a) harboring an IPTG-inducible expression plasmid containing BAP1 or an enzymatically null mutant, BAP1 (C91 S) (pQE-30; QIAGEN Inc.) were grown and induced with 1 mM IPTG for 4 hours. The bacteria were collected and the pellets were resuspended to 1/20 volume (original culture) in lysate buffer (50 mM Tris, pH 8.0, 25 mM EDTA, 10 mM 2-mercaptoethanol, 100 μg/ml lysozyme). The lysates were sonicated and centrifuged at 40,000×g.

The pellets were resuspended in an volume equal to that of the supernatant and samples of both pellet and supernatant were analyzed by SDS-PAGE for expression levels and inclusion body formation. Induction of protein was verified by SDS-PAGE of each fraction. Overexpression of BAP1 in bacteria led to abundant protein, most of which was found in an inactive, insoluble form.

Assays for BAP1 enzymatic activity, specifically, ubiquitin carboxy-terminal hydrolase activity, were performed on the above-described soluble fraction essentially as described for the UCH-L1 and UCH-L3 enzymes using the glycine 76 ethyl ester of ubiquitin (Ub-OEt) as a substrate [Mayer et al, cited above; Wilkinson et al, *Biochemistry*, 25:6644–6649 (1986)]. Assays were done in triplicate. The peak areas were integrated and normalized with respect to a ubiquitin standard.

The BAP1 protein found in the soluble fraction was able to hydrolyze UbOEt and the level of this activity increased with the level of protein, indicating that BAP1 contains UCH-like enzymatic activity.

The active site thiol residue responsible for UCH activity in UCH-L3 has been identified and its mutation leads to abolition of enzyme activity [Larsen et al, cited above]. Mutation of the corresponding cysteine residue in BAP1, BAP1 (C91 S), yielded a protein with no UCH activity, further suggesting that BAP1 is a thiol protease of the UCH family.

BAP1's identity as a protease of the ubiquitin carboxy-terminal hydrolase (UCH) family implies a role for either ubiguitin-mediated, proteasome dependent degradation or other ubiquitin-mediated regulatory [Isaksson et al, *Biochimica et Biophysica Acta*, 1288:F21–29 (1996)] pathways in BRCA1 function. Regulated ubiquitination of proteins and subsequent proteasome-dependent proteolysis plays a role in almost every cellular growth, differentiation and homeostatic process (reviewed by Ciechanover, *Biol. Chem. Hoppe-Seyler*, 375:565–581 (1994); Isaksson et al, cited above; Wilkinson, *Annual Review of Nutrition*, 15:161–189 (1995)]. This pathway can be broadly subdivided into reactions involving 1) pro-ubiquitin processing and ATP-dependent activation of ubiquiting; 2) substrate recognition, conjugation and editing of the polyubiquitin chain; 3) proteasome-dependent degradation of the ubiquitin protein and; 4) cleavage and/or debranching of peptide-ubiquitin conjugates and recycling of ubiquitin to cellular pools. The pathway is regulated at almost every step. First, at the level of substrate specificity via the concerted actions of activating enzymes, carrier proteins and ligation enzymes, and secondly, at the level of proteolytic deubiquitination and ubiquitin hydrolysis.

The UCH family has been characterized as a set of small (25–30 kDa) cytoplasmic proteins which prefer to cleave ubiquitin from ubiquitin-conjugated small substrates and may also be involved in the co-translational processing of proubiquitin. UCHs show considerable tissue specificity and developmentally-timed regulation [Wilkinson et al, *Biochem. Soc. Trans.*, 20:631–637 (1992)]. UCH family members are strongly and differentially expressed in neuronal, hematopoietic and germ cells in many species. Most remarkably, a novel UCH enzyme has recently been cloned from Aplysia californica whose enzymatic function is essential for acquisition and maintenance of long-term memory [Hedge et al, *Cell*, 89:114–126 (1997)]. Finally, UCH levels are strongly downregulated during viral transformation of fibroblasts [Honore et al, *FEBS Letter*, 280:235–240 (1991)], consistent with a role in growth control.

BAP1 is the newest member of the UCH family and considerably expands the potential roles of this family of proteases. BAP1 is a much larger protein (90 kDa) and is the first nuclear-localized UCH. BAP1 is also likely to be involved in the regulation of protein subcellular localization. Ubiquitin, or a ubiquitin-like moiety, may affect the specific targeting of proteins to locations other than the proteasome [see, e.g., Mahajan et al, *Cell*, 88:97–107 (1997)]. BAP1-mediated removal of "ubiquitin" from BRCA1, or a protein associated with BRCA1, could target it for removal to another cellular compartment, thus functionally destroying the protein without physically doing so.

BRCA1 is also localized in nuclear dot structures in a cell-cycle dependent manner [Scully et al, cited above]. This association of BRCA1 with RAD51 in both mitotic and meiotic cells broadly implicates BRCA1 in DNA repair and/or recombination processes. The RAD51/52-dependent DNA repair pathway is highly regulated and includes many proteins, some of which may be potential substrates for BAP1-mediated ubiquitin hydrolysis [Watkins et al, *Molecular & Cellular Biology*, 13:7757–7765 (1993)]. Thus, it appears that the DNA repair machinery contains both ubiquitin-conjugating and -hydrolyzing elements, since BAP1 is now implicated as a member of the BRCA1/RAD51/hUBC9 complex. It is possible that BAP1, which is co-expressed with BRCA1 in testis, may regulate the recombination/repair functions of the BRCA1/RAD52 complex by targeting either RAD23 or UBL1 for ubiquitin hydrolysis.

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A nucleic acid sequence encoding mammalian BRCA1 Associated Protein (BAP-1) comprising nucleotides 40–2226 of SEQ ID NO: 1, or a sequence completely complementary thereto, isolated from cellular materials with which it is naturally associated.

2. An isolated fragment of a nucleic acid sequence encoding mammalian BRCA1 Associated Protein (BAP-1), wherein said fragment is selected from the group consisting of:

(a) an interactive domain, nucleotides 1831 to 2226 of SEQ ID NO: 1; and (b) a sequence completely complementary to the sequence of (a).

3. The sequence according to claim 1 which encodes human BAP-1 amino acid numbers 1 to 729 of SEQ ID NO: 2.

4. A recombinant molecule including a mammalian nucleic acid sequence encoding a BRCA1 associated protein (BAP-1) or peptide, said nucleic acid sequence comprising nucleotides 40–2226 of SEQ ID NO: 1 under the control of regulatory sequences, which permit expression of the BAP-1 protein or peptide in a host cell.

5. A host cell transformed with the recombinant molecule according to claim 4.

6. A method of recombinantly expressing BRCA1 associated protein (BAP-1) comprising culturing a recombinant host cell transformed with a nucleic acid sequence comprising nucleotides 40–2226 of SEQ ID NO: 1 under conditions which permit expression of BAP-1.

7. A reagent including an isolated or recombinant nucleic acid sequence selected from the group consisting of:

(a) SEQ ID NO: 1;

(b) a nucleotide sequence containing nucleotides 40 to 2226 of SEQ ID NO: 1;

(c) a nucleotide sequence consisting of a nucleotide sequence encoding amino acids 598 to 729 of SEQ ID NO: 2;

(d) a sequence completely complementary to a sequence of (a) through (c);

and a detectable label which is bound to said sequence.

8. A composition comprising an isolated or recombinant nucleic acid molecule selected from the group consisting of (a) a plasmid comprising a nucleic acid sequence encoding a BAP-1 protein or peptide, said nucleic acid sequence comprising nucleotides 40–2226 of SEQ ID NO: 1 under the control of regulatory sequences directing expression of the encoded protein or peptide in a host cell;

(b) a virus vector comprising a nucleic acid sequence encoding a BAP-1 protein or peptide, said nucleic acid sequence comprising nucleotides 40–2226 of SEQ ID NO: 1 under the control of regulatory sequence directing expression of the encoded protein or peptide in a host cell;

and a pharmaceutically acceptable carrier.

9. A recombinant molecule including a nucleic acid sequence selected from the group consisting of (a) SEQ ID NO: 1;

(b) a nucleotide sequence containing nucleotides 40 to 2226 of SEQ ID NO: 1;

(c) a nucleotide sequence consisting of a nucleotide sequence encoding amino acids 598 to 729 of SEQ ID NO: 2; and (d) a sequence completely complementary to a sequence of (a) through (c);

and a detectable label.

10. A plasmid comprising a nucleic acid sequence encoding a BAP-1 protein or peptide, said nucleic acid sequence comprising nucleotides 40–2226 of SEQ ID NO: 1 under the control of regulatory sequences directing expression of the encoded protein or peptide in a host cell.

11. A virus vector comprising a nucleic acid sequence encoding a BAP-1 protein or peptide, said nucleic acid sequence comprising nucleotides 40–2226 of SEQ ID NO: 1 under the control of regulatory sequence directing expression of the encoded protein or peptide in a host cell.

* * * * *

SEQUENCE LISTING (1) GENERAL INFORMATION:

(iii) NUMBER OF SEQUENCES: 47

(2) INFORMATION FOR SEQ ID NO:1:

(i) SEQUENCE CHARACTERISTICS:
      (A) LENGTH: 3517 base pairs
      (B) TYPE: nucleic acid
      (C) STRANDEDNESS: double
      (D) TOPOLOGY: Not Relevant (ii) MOLECULE TYPE: cDNA (ix) FEATURE:
      (A) NAME/KEY: CDS
      (B) LOCATION: 40..2226

(xi) SEQUENCE DESCRIPTION: SEQ ID NO:1:

```
GGCACGAGGC ATGGCGCTGA GGGGCCGCCC CGCGGGAAG ATG AAT AAG GGC TGG         54
                                            Met Asn Lys Gly Trp
                                              1               5

CTG GAG CTG GAG AGC GAC CCA GGC CTC TTC ACC CTG CTC GTG GAA GAT       102
Leu Glu Leu Glu Ser Asp Pro Gly Leu Phe Thr Leu Leu Val Glu Asp
             10                  15                  20

TTC GGT GTC AAG GGG GTG CAA GTG GAG GAG ATC TAC GAC CTT CAG AGC       150
Phe Gly Val Lys Gly Val Gln Val Glu Glu Ile Tyr Asp Leu Gln Ser
         25                  30                  35

AAA TGT CAG GGC CCT GTA TAT GGA TTT ATC TTC CTG TTC AAA TGG ATC       198
Lys Cys Gln Gly Pro Val Tyr Gly Phe Ile Phe Leu Phe Lys Trp Ile
     40                  45                  50

GAA GAG CGC CGG TCC CGG CGA AAG GTC TCT ACC TTG GTG GAT GAT ACG       246
Glu Glu Arg Arg Ser Arg Arg Lys Val Ser Thr Leu Val Asp Asp Thr
 55                  60                  65

TCC GTG ATT GAT GAT GAT ATT GTG AAT AAC ATG TTC TTT GCC CAC CAG       294
Ser Val Ile Asp Asp Asp Ile Val Asn Asn Met Phe Phe Ala His Gln
 70                  75                  80                  85

CTG ATA CCC AAC TCT TGT GCA ACT CAT GCC TTG CTG AGC GTG CTC CTG       342
Leu Ile Pro Asn Ser Cys Ala Thr His Ala Leu Leu Ser Val Leu Leu
                 90                  95                 100

AAC TGC AGC AGC GTG GAC CTG GGA CCC ACC CTG AGT CGC ATG AAG GAC       390
Asn Cys Ser Ser Val Asp Leu Gly Pro Thr Leu Ser Arg Met Lys Asp
            105                 110                 115

TTC ACC AAG GGT TTC AGC CCT GAG AGC AAA GGA TAT GCG ATT GGC AAT       438
Phe Thr Lys Gly Phe Ser Pro Glu Ser Lys Gly Tyr Ala Ile Gly Asn
        120                 125                 130

GCC CCG GAG TTG GCC AAG GCC CAT AAT AGC CAT GCC AGG CCC GAG CCA       486
Ala Pro Glu Leu Ala Lys Ala His Asn Ser His Ala Arg Pro Glu Pro
    135                 140                 145

CGC CAC CTC CCT GAG AAG CAG AAT GGC CTT AGT GCA GTG CGG ACC ATG       534
Arg His Leu Pro Glu Lys Gln Asn Gly Leu Ser Ala Val Arg Thr Met
150                 155                 160                 165

GAG GCG TTC CAC TTT GTC AGC TAT GTG CCT ATC ACA GGC CGG CTC TTT       582
Glu Ala Phe His Phe Val Ser Tyr Val Pro Ile Thr Gly Arg Leu Phe
                170                 175                 180

GAG CTG GAT GGG CTG AAG GTC TAC CCC ATT GAC CAT GGG CCC TGG GGG       630
Glu Leu Asp Gly Leu Lys Val Tyr Pro Ile Asp His Gly Pro Trp Gly
            185                 190                 195

GAG GAC GAG GAG TGG ACA GAC AAG GCC CGG CGG GTC ATC ATG GAG CGT       678
Glu Asp Glu Glu Trp Thr Asp Lys Ala Arg Arg Val Ile Met Glu Arg
        200                 205                 210
```

```
ATC GGC CTC GCC ACT GCA GGG GAG CCC TAC CAC GAC ATC CGC TTC AAC      726
Ile Gly Leu Ala Thr Ala Gly Glu Pro Tyr His Asp Ile Arg Phe Asn
    215                 220                 225

CTG ATG GCA GTG GTG CCC GAC CGC AGG ATC AAG TAT GAG GCC AGG CTG      774
Leu Met Ala Val Val Pro Asp Arg Arg Ile Lys Tyr Glu Ala Arg Leu
230                 235                 240                 245

CAT GTG CTG AAG GTG AAC CGT CAG ACA GTA CTA GAG GCT CTG CAG CAG      822
His Val Leu Lys Val Asn Arg Gln Thr Val Leu Glu Ala Leu Gln Gln
                250                 255                 260

CTG ATA AGA GTA ACA CAG CCA GAG CTG ATT CAG ACC CAC AAG TCT CAA      870
Leu Ile Arg Val Thr Gln Pro Glu Leu Ile Gln Thr His Lys Ser Gln
            265                 270                 275

GAG TCA CAG CTG CCT GAG GAG TCC AAG TCA GCC AGC AAC AAG TCC CCG      918
Glu Ser Gln Leu Pro Glu Glu Ser Lys Ser Ala Ser Asn Lys Ser Pro
        280                 285                 290

CTG GTG CTG GAA GCA AAC AGG GCC CCT GCA GCC TCT GAG GGC AAC CAC      966
Leu Val Leu Glu Ala Asn Arg Ala Pro Ala Ala Ser Glu Gly Asn His
    295                 300                 305

ACA GAT GGT GCA GAG GAG GCG GCT GGT TCA TGC GCA CAA GCC CCA TCC     1014
Thr Asp Gly Ala Glu Glu Ala Ala Gly Ser Cys Ala Gln Ala Pro Ser
310                 315                 320                 325

CAC AGC CCT CCC AAC AAA CCC AAG CTA GTG GTG AAG CCT CCA GGC AGC     1062
His Ser Pro Pro Asn Lys Pro Lys Leu Val Val Lys Pro Pro Gly Ser
                330                 335                 340

AGC CTC AAT GGG GTT CAC CCC AAC CCC ACT CCC ATT GTC CAG CGG CTG     1110
Ser Leu Asn Gly Val His Pro Asn Pro Thr Pro Ile Val Gln Arg Leu
            345                 350                 355

CCG GCC TTT CTA GAC AAT CAC AAT TAT GCC AAG TCC CCC ATG CAG GAG     1158
Pro Ala Phe Leu Asp Asn His Asn Tyr Ala Lys Ser Pro Met Gln Glu
        360                 365                 370

GAA GAA GAC CTG GCG GCA GGT GTG GGC CGC AGC CGA GTT CCA GTC CGC     1206
Glu Glu Asp Leu Ala Ala Gly Val Gly Arg Ser Arg Val Pro Val Arg
    375                 380                 385

CCA CCC CAG CAG TAC TCA GAT GAT GAG GAT GAC TAT GAG GAT GAC GAG     1254
Pro Pro Gln Gln Tyr Ser Asp Asp Glu Asp Asp Tyr Glu Asp Asp Glu
390                 395                 400                 405

GAG GAT GAC GTG CAG AAC ACC AAC TCT GCC CTT AGG TAT AAG GGG AAG     1302
Glu Asp Asp Val Gln Asn Thr Asn Ser Ala Leu Arg Tyr Lys Gly Lys
                410                 415                 420

GGA ACA GGG AAG CCA GGG GCA TTG AGC GGT TCT GCT GAT GGG CAA CTG     1350
Gly Thr Gly Lys Pro Gly Ala Leu Ser Gly Ser Ala Asp Gly Gln Leu
            425                 430                 435

TCA GTG CTG CAG CCC AAC ACC ATC AAC GTC TTG GCT GAG AAG CTC AAA     1398
Ser Val Leu Gln Pro Asn Thr Ile Asn Val Leu Ala Glu Lys Leu Lys
        440                 445                 450

GAG TCC CAG AAG GAC CTC TCA ATT CCT CTG TCC ATC AAG ACT AGC AGC     1446
Glu Ser Gln Lys Asp Leu Ser Ile Pro Leu Ser Ile Lys Thr Ser Ser
    455                 460                 465

GGG GCT GGG AGT CCG GCT GTG GCA GTG CCC ACA CAC TCG CAG CCC TCA     1494
Gly Ala Gly Ser Pro Ala Val Ala Val Pro Thr His Ser Gln Pro Ser
470                 475                 480                 485

CCC ACC CCC AGC AAT GAG AGT ACA GAC ACG GCC TCT GAG ATC GGC AGT     1542
Pro Thr Pro Ser Asn Glu Ser Thr Asp Thr Ala Ser Glu Ile Gly Ser
                490                 495                 500

GCT TTC AAC TCG CCA CTG CGC TCG CCT ATC CGC TCA GCC AAC CCG ACG     1590
Ala Phe Asn Ser Pro Leu Arg Ser Pro Ile Arg Ser Ala Asn Pro Thr
            505                 510                 515

CGG CCC TCC AGC CCT GTC ACC TCC CAC ATC TCC AAG GTG CTT TTT GGA     1638
Arg Pro Ser Ser Pro Val Thr Ser His Ile Ser Lys Val Leu Phe Gly
```

```
                520                 525                 530
GAG GAT GAC AGC CTG CTG CGT GTT GAC TGC ATA CGC TAC AAC CGT GCT    1686
Glu Asp Asp Ser Leu Leu Arg Val Asp Cys Ile Arg Tyr Asn Arg Ala
        535                 540                 545

GTC CGT GAT CTG GGT CCT GTC ATC AGC ACA GGC CTG CTG CAC CTG GCT    1734
Val Arg Asp Leu Gly Pro Val Ile Ser Thr Gly Leu Leu His Leu Ala
550                 555                 560                 565

GAG GAT GGG GTG CTG AGT CCC CTG GCG CTG ACA GAG GGT GGG AAG GGT    1782
Glu Asp Gly Val Leu Ser Pro Leu Ala Leu Thr Glu Gly Gly Lys Gly
                570                 575                 580

TCC TCG CCC TCC ATC AGA CCA ATC CAA GGC AGC CAG GGG TCC AGC AGC    1830
Ser Ser Pro Ser Ile Arg Pro Ile Gln Gly Ser Gln Gly Ser Ser Ser
            585                 590                 595

CCA GTG GAG AAG GAG GTC GTG GAA GCC ACG GAC AGC AGA GAG AAG ACG    1878
Pro Val Glu Lys Glu Val Val Glu Ala Thr Asp Ser Arg Glu Lys Thr
        600                 605                 610

GGG ATG GTG AGG CCT GGC GAG CCC TTG AGT GGG GAG AAA TAC TCA CCC    1926
Gly Met Val Arg Pro Gly Glu Pro Leu Ser Gly Glu Lys Tyr Ser Pro
    615                 620                 625

AAG GAG CTG CTG GCA CTG CTG AAG TGT GTG GAG GCT GAG ATT GCA AAC    1974
Lys Glu Leu Leu Ala Leu Leu Lys Cys Val Glu Ala Glu Ile Ala Asn
630                 635                 640                 645

TAT GAG GCG TGC CTC AAG GAG GAG GTA GAG AAG AGG AAG AAG TTC AAG    2022
Tyr Glu Ala Cys Leu Lys Glu Glu Val Glu Lys Arg Lys Lys Phe Lys
                650                 655                 660

ATT GAT GAC CAG AGA AGG ACC CAC AAC TAC GAT GAG TTC ATC TGC ACC    2070
Ile Asp Asp Gln Arg Arg Thr His Asn Tyr Asp Glu Phe Ile Cys Thr
            665                 670                 675

TTT ATC TCC ATG CTG GCT CAG GAA GGC ATG CTG GCC AAC CTA GTG GAG    2118
Phe Ile Ser Met Leu Ala Gln Glu Gly Met Leu Ala Asn Leu Val Glu
        680                 685                 690

CAG AAC ATC TCC GTG CGG CGG CGC CAA GGG GTC AGC ATC GGC CGG CTC    2166
Gln Asn Ile Ser Val Arg Arg Arg Gln Gly Val Ser Ile Gly Arg Leu
    695                 700                 705

CAC AAG CAG CGG AAG CCT GAC CGG CGG AAA CGC TCT CGC CCC TAC AAG    2214
His Lys Gln Arg Lys Pro Asp Arg Arg Lys Arg Ser Arg Pro Tyr Lys
710                 715                 720                 725

GCC AAG CGC CAG TGAGGACTGC TGGCCCTGAC TCTGCAGCCC ACTCTTGCCG        2266
Ala Lys Arg Gln

TGTGGCCCTC ACCAGGGTCC TTCCCTGCCC CACTTCCCCT TTTCCCAGTA TTACTGAATA    2326

GTCCCAGCTG GAGAGTCCAG GCCCTGGGAA TGGGAGGAAC CAGGCCACAT TCCTTCCATC    2386

GTGCCCTGAG GCCTGACACG GCAGATCAGC CCCATAGTGC TCAGGAGGCA GCATCTGGAG    2446

TTGGGGCACA GCGAGGTACT GCAGCTTCCT CCACAGCCGG CTGTGGAGCA GCAGGACCTG    2506

GCCCTTCTGC CTGGGCAGCA GAATATATAT TTTACCTATC AGAGACATCT ATTTTTCTGG    2566

GCTCCAACCC AACATGCCAC CATGTTGACA TAAGTTCCTA CCTGACTATG CTTTCTCTCC    2626

TAGGAGCTGT CCTGGTGGGC CCAGGTCCTT GTATCATCCA CGGTCCCAAC TACAGGGTCC    2686

TAGCTGGGGG CCTGGGTGGG CCCTGGGCTC TGGGCCCTGC TGCTCTAGCC CCAGCCACCA    2746

GCCTGTCCCT GTTGTAAGGA AGCCAGGTCT TCTCTCTTCA TTCCTCTTAG GAGAGTGCCA    2806

AACTCAGGGA CCCAGCACTG GGCTGGGTTG GGAGTAGGGT GTCCCAGTGG GGTTGGGGTG    2866

AGCAGGCTGC TGGGATCCCA TGGCCTGAGC AGAGCATGTG GGAACTGTTC AGTGGCCTGT    2926

GAACTGTCTT CCTTGTTCTA GCCAGGCTGT TCAAGACTGC TCTCCATAGC AAGGTTCTAG    2986

GGCTCTTCGC CTTCAGTGTT GTGGCCCTAG CTATGGGCCT AAATTGGGCT CTAGGTCTCT    3046
```

-continued

```
GTCCCTGGCG CTTGAGGCTC AGAAGAGCCT CTGTCCAGCC CCTCAGTATT ACCATGTCTC    3106

CCTCTCAGGG GTAGCAGAGA CAGGGTTGCT TATAGGAAGC TGGCACCACT CAGCTCTTCC    3166

TGCTACTCCA GTTTCCTCAG CCTCTGCAAG GCACTCAGGG TGGGGACAG CAGGATCAAG     3226

ACAACCCGTT GGAGCCCCTG TGTTCCAGAG GACCTGATGC CAAGGGGTAA TGGGCCCAGC    3286

AGTGCCTCTG GAGCCCAGGC CCCAACACAG CCCCATGGCC TCTCCAGATG GCTTTGAAAA    3346

GGTGATCCAA CAGGCCCCTT TATCTGTACA TAGTGACTGA GTGGGGGGTG CTGGCAAGTG    3406

TGGCACTCCT CTGGGCTGAG CACAGCTTGA CCCCTCTAGC CCCTGTAAAA CTGGATCAAT    3466

GAATGAATAA AACTCTCCTA AGATCTCCTG AGAAAAAAAA AAAAAAAAAG               3517
```

(2) INFORMATION FOR SEQ ID NO:2:

(i) SEQUENCE CHARACTERISTICS:
 (A) LENGTH: 729 amino acids
 (B) TYPE: amino acid
 (D) TOPOLOGY: linear (ii) MOLECULE TYPE: protein (xi) SEQUENCE DESCRIPTION: SEQ ID NO:2:

```
Met Asn Lys Gly Trp Leu Glu Leu Glu Ser Asp Pro Gly Leu Phe Thr
 1               5                  10                  15

Leu Leu Val Glu Asp Phe Gly Val Lys Gly Val Gln Val Glu Glu Ile
                20                  25                  30

Tyr Asp Leu Gln Ser Lys Cys Gln Gly Pro Val Tyr Gly Phe Ile Phe
            35                  40                  45

Leu Phe Lys Trp Ile Glu Glu Arg Ser Arg Arg Lys Val Ser Thr
         50                  55                  60

Leu Val Asp Asp Thr Ser Val Ile Asp Asp Ile Val Asn Asn Met
 65                  70                  75                  80

Phe Phe Ala His Gln Leu Ile Pro Asn Ser Cys Ala Thr His Ala Leu
                85                  90                  95

Leu Ser Val Leu Leu Asn Cys Ser Ser Val Asp Leu Gly Pro Thr Leu
            100                 105                 110

Ser Arg Met Lys Asp Phe Thr Lys Gly Phe Ser Pro Glu Ser Lys Gly
        115                 120                 125

Tyr Ala Ile Gly Asn Ala Pro Glu Leu Ala Lys Ala His Asn Ser His
    130                 135                 140

Ala Arg Pro Glu Pro Arg His Leu Pro Glu Lys Gln Asn Gly Leu Ser
145                 150                 155                 160

Ala Val Arg Thr Met Glu Ala Phe His Phe Val Ser Tyr Val Pro Ile
                165                 170                 175

Thr Gly Arg Leu Phe Glu Leu Asp Gly Leu Lys Val Tyr Pro Ile Asp
            180                 185                 190

His Gly Pro Trp Gly Glu Asp Glu Trp Thr Asp Lys Ala Arg Arg
        195                 200                 205

Val Ile Met Glu Arg Ile Gly Leu Ala Thr Ala Gly Glu Pro Tyr His
    210                 215                 220

Asp Ile Arg Phe Asn Leu Met Ala Val Val Pro Asp Arg Arg Ile Lys
225                 230                 235                 240

Tyr Glu Ala Arg Leu His Val Leu Lys Val Asn Arg Gln Thr Val Leu
                245                 250                 255

Glu Ala Leu Gln Gln Leu Ile Arg Val Thr Gln Pro Glu Leu Ile Gln
            260                 265                 270
```

-continued

```
Thr His Lys Ser Gln Glu Ser Gln Leu Pro Glu Glu Ser Lys Ser Ala
        275                 280                 285

Ser Asn Lys Ser Pro Leu Val Leu Glu Ala Asn Arg Ala Pro Ala Ala
        290                 295                 300

Ser Glu Gly Asn His Thr Asp Gly Ala Glu Glu Ala Ala Gly Ser Cys
305                 310                 315                 320

Ala Gln Ala Pro Ser His Ser Pro Pro Asn Lys Pro Lys Leu Val Val
                325                 330                 335

Lys Pro Pro Gly Ser Ser Leu Asn Gly Val His Pro Asn Pro Thr Pro
                340                 345                 350

Ile Val Gln Arg Leu Pro Ala Phe Leu Asp Asn His Asn Tyr Ala Lys
                355                 360                 365

Ser Pro Met Gln Glu Glu Asp Leu Ala Ala Gly Val Gly Arg Ser
        370                 375                 380

Arg Val Pro Val Arg Pro Pro Gln Gln Tyr Ser Asp Asp Glu Asp Asp
385                 390                 395                 400

Tyr Glu Asp Asp Glu Glu Asp Val Gln Asn Thr Asn Ser Ala Leu
                405                 410                 415

Arg Tyr Lys Gly Lys Gly Thr Gly Lys Pro Gly Ala Leu Ser Gly Ser
                420                 425                 430

Ala Asp Gly Gln Leu Ser Val Leu Gln Pro Asn Thr Ile Asn Val Leu
                435                 440                 445

Ala Glu Lys Leu Lys Glu Ser Gln Lys Asp Leu Ser Ile Pro Leu Ser
        450                 455                 460

Ile Lys Thr Ser Ser Gly Ala Gly Ser Pro Ala Val Ala Val Pro Thr
465                 470                 475                 480

His Ser Gln Pro Ser Pro Thr Pro Ser Asn Glu Ser Thr Asp Thr Ala
                485                 490                 495

Ser Glu Ile Gly Ser Ala Phe Asn Ser Pro Leu Arg Ser Pro Ile Arg
                500                 505                 510

Ser Ala Asn Pro Thr Arg Pro Ser Ser Pro Val Thr Ser His Ile Ser
                515                 520                 525

Lys Val Leu Phe Gly Glu Asp Asp Ser Leu Leu Arg Val Asp Cys Ile
        530                 535                 540

Arg Tyr Asn Arg Ala Val Arg Asp Leu Gly Pro Val Ile Ser Thr Gly
545                 550                 555                 560

Leu Leu His Leu Ala Glu Asp Gly Val Leu Ser Pro Leu Ala Leu Thr
                565                 570                 575

Glu Gly Gly Lys Gly Ser Ser Pro Ser Ile Arg Pro Ile Gln Gly Ser
                580                 585                 590

Gln Gly Ser Ser Ser Pro Val Glu Lys Glu Val Val Glu Ala Thr Asp
        595                 600                 605

Ser Arg Glu Lys Thr Gly Met Val Arg Pro Gly Glu Pro Leu Ser Gly
        610                 615                 620

Glu Lys Tyr Ser Pro Lys Glu Leu Leu Ala Leu Leu Lys Cys Val Glu
625                 630                 635                 640

Ala Glu Ile Ala Asn Tyr Glu Ala Cys Leu Lys Glu Val Glu Lys
                645                 650                 655

Arg Lys Lys Phe Lys Ile Asp Asp Gln Arg Arg Thr His Asn Tyr Asp
                660                 665                 670

Glu Phe Ile Cys Thr Phe Ile Ser Met Leu Ala Gln Glu Gly Met Leu
                675                 680                 685

Ala Asn Leu Val Glu Gln Asn Ile Ser Val Arg Arg Arg Gln Gly Val
```

-continued

```
            690                 695                 700
Ser Ile Gly Arg Leu His Lys Gln Arg Lys Pro Asp Arg Lys Arg
705                 710                 715                 720

Ser Arg Pro Tyr Lys Ala Lys Arg Gln
                725
```

(2) INFORMATION FOR SEQ ID NO:3:

(i) SEQUENCE CHARACTERISTICS:
        (A) LENGTH: 100 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:3:

```
Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
                20                  25                  30

Glu Pro Val Ser Thr Lys Cys Asp His Ile Phe Cys Lys Phe Cys Met
            35                  40                  45

Leu Lys Leu Leu Asn Gln Lys Lys Gly Pro Ser Gln Cys Pro Leu Cys
50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
                85                  90                  95

Thr Gly Leu Glu
            100
```

(2) INFORMATION FOR SEQ ID NO:4:

(i) SEQUENCE CHARACTERISTICS:
        (A) LENGTH: 100 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:4:

```
Met Asp Leu Ser Ala Val Gln Ile Gln Glu Val Gln Asn Val Leu His
1               5                   10                  15

Ala Met Gln Lys Ile Leu Glu Cys Pro Ile Cys Leu Glu Leu Ile Lys
                20                  25                  30

Glu Pro Val Ser Thr Lys Cys Asp His Ile Phe Cys Lys Phe Cys Met
            35                  40                  45

Leu Lys Leu Leu Asn Gln Lys Lys Gly Pro Ser Gln Cys Pro Leu Cys
50                  55                  60

Lys Asn Glu Ile Thr Lys Arg Ser Leu Gln Gly Ser Thr Arg Phe Ser
65                  70                  75                  80

Gln Leu Ala Glu Glu Leu Leu Arg Ile Met Ala Ala Phe Glu Leu Asp
                85                  90                  95

Thr Gly Met Gln
            100
```

(2) INFORMATION FOR SEQ ID NO:5:

```
       (i) SEQUENCE CHARACTERISTICS:
           (A) LENGTH: 100 amino acids
           (B) TYPE: amino acid
           (C) STRANDEDNESS:
           (D) TOPOLOGY: unknown (ii) MOLECULE TYPE: protein (xi) SEQUENCE DESCRIPTION: SEQ ID NO:5:

Met Ala Ser Ser Val Leu Glu Met Ile Lys Glu Val Thr Cys Pro
1               5                  10                  15

Ile Cys Leu Glu Leu Leu Lys Glu Pro Val Ser Ala Asp Cys Asn His
               20                  25                  30

Ser Phe Cys Arg Ala Cys Ile Thr Leu Asn Tyr Glu Ser Asn Arg Asn
               35                  40                  45

Thr Asp Gly Lys Gly Asn Cys Pro Val Cys Arg Val Pro Tyr Pro Phe
           50                  55                  60

Gly Asn Leu Arg Pro Asn Leu His Val Ala Asn Ile Val Glu Arg Leu
65                  70                  75                  80

Lys Gly Phe Lys Ser Ile Pro Glu Glu Glu Gln Lys Val Asn Ile Cys
                85                  90                  95

Ala Gln His Gly
            100

(2) INFORMATION FOR SEQ ID NO:6:

(i) SEQUENCE CHARACTERISTICS:
           (A) LENGTH: 262 amino acids
           (B) TYPE: amino acid
           (C) STRANDEDNESS:
           (D) TOPOLOGY: unknown (ii) MOLECULE TYPE: protein (xi) SEQUENCE DESCRIPTION: SEQ ID NO:6:

Lys Lys Glu Ile Trp Asn Ser Asp Pro Arg Gly His Glu Gly Pro Gln
1               5                  10                  15

Pro Ser Pro Thr Pro Ser Asn Glu Ser Thr Asp Thr Ala Ser Glu Ile
               20                  25                  30

Gly Ser Ala Phe Asn Ser Pro Leu Arg Ser Pro Ile Arg Ser Ala Asn
               35                  40                  45

Pro Thr Arg Pro Ser Ser Pro Val Thr Ser His Ile Ser Lys Val Leu
           50                  55                  60

Phe Gly Glu Asp Asp Ser Leu Leu Arg Val Asp Cys Ile Arg Tyr Asn
65                  70                  75                  80

Arg Ala Val Arg Asp Leu Gly Pro Val Ile Ser Thr Gly Leu Leu His
                85                  90                  95

Leu Ala Glu Asp Gly Val Leu Ser Pro Leu Ala Leu Thr Glu Gly Gly
            100                 105                 110

Lys Gly Ser Ser Pro Ser Ile Arg Pro Ile Gln Gly Ser Gln Gly Ser
            115                 120                 125

Ser Ser Pro Val Glu Lys Val Val Glu Ala Thr Asp Ser Arg Glu
130                 135                 140

Lys Thr Gly Met Val Arg Ser Gly Glu Pro Leu Ser Gly Glu Lys Tyr
145                 150                 155                 160

Ser Pro Lys Glu Leu Leu Ala Leu Leu Lys Cys Val Glu Ala Glu Ile
                165                 170                 175

Ala Asn Tyr Glu Ala Cys Leu Lys Glu Glu Val Glu Lys Arg Lys Lys
            180                 185                 190
```

```
Phe Lys Ile Asp Asp Gln Arg Arg Thr His Asn Tyr Asp Glu Phe Ile
        195                 200                 205

Cys Thr Phe Ile Ser Met Leu Ala Gln Glu Gly Met Leu Ala Asn Leu
        210                 215                 220

Val Glu Gln Asn Ile Ser Val Arg Arg Gln Gly Val Ser Ile Gly
225                 230                 235                 240

Arg Leu His Lys Gln Arg Lys Pro Asp Arg Arg Lys Arg Ser Arg Pro
                245                 250                 255

Tyr Lys Ala Lys Arg Gln
            260
```

(2) INFORMATION FOR SEQ ID NO:7:

(i) SEQUENCE CHARACTERISTICS:
        (A) LENGTH: 188 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:7:

```
Gly Gly Ile Asp Trp Ile Pro Gly Tyr Arg Ala Gln Ile Arg Arg Pro
1               5                   10                  15

Ser Ser Pro Val Thr Ser His Ile Ser Lys Val Leu Phe Gly Glu Asp
            20                  25                  30

Asp Ser Leu Leu Arg Val Asp Cys Ile Arg Tyr Asn Arg Ala Val Arg
            35                  40                  45

Asp Leu Gly Pro Val Ile Ser Thr Gly Leu Leu His Leu Ala Glu Asp
50                  55                  60

Gly Val Leu Ser Pro Leu Ala Leu Thr Glu Gly Gly Lys Gly Ser Ser
65                  70                  75                  80

Pro Ser Thr Arg Ser Ser Gln Gly Ser Gln Gly Ser Ser Gly Leu Glu
                85                  90                  95

Glu Lys Glu Val Val Glu Val Thr Glu Ser Arg Asp Lys Pro Gly Leu
                100                 105                 110

Asn Arg Ser Ser Glu Pro Leu Ser Gly Glu Lys Tyr Ser Pro Lys Ile
            115                 120                 125

Asp Asp Gln Arg Arg Thr His Asn Tyr Asp Glu Phe Ile Cys Thr Phe
130                 135                 140

Ile Ser Met Leu Ala Gln Glu Gly Met Leu Ala Asn Leu Val Glu Gln
145                 150                 155                 160

Asn Ile Ser Val Arg Arg Gln Gly Val Ser Ile Gly Arg Leu His
                165                 170                 175

Lys Gln Arg Lys Pro Asp Arg Arg Met Ser Gly Arg
            180                 185
```

(2) INFORMATION FOR SEQ ID NO:8:

(i) SEQUENCE CHARACTERISTICS:
        (A) LENGTH: 161 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:8:

Gly Gly Ile Asp Trp Ile Pro Gly Val Arg Ala Gln Ile Arg Pro Ile

```
1               5                   10                  15
Ser Ser Ser Ser Pro Ser Thr Arg Ser Ser Gln Gly Ser Gln Gly Ser
                20                  25              30
Ser Gly Leu Glu Glu Lys Glu Val Val Glu Val Thr Glu Ser Arg Asp
            35                  40                  45
Lys Pro Gly Leu Asn Arg Ser Ser Glu Pro Leu Ser Gly Glu Lys Tyr
    50                  55                  60
Ser Pro Lys Glu Leu Leu Ala Leu Leu Lys Cys Ala Glu Ala Glu Ile
65                  70                  75                  80
Ala Asn Tyr Glu Ala Cys Leu Lys Glu Glu Val Glu Lys Arg Lys Lys
                85                  90                  95
Phe Lys Ile Asp Asp Gln Arg Arg Thr His Asn Tyr Asp Glu Phe Ile
                100                 105                 110
Cys Thr Phe Ile Ser Met Leu Ala Gln Glu Gly Met Leu Ala Asn Leu
            115                 120                 125
Val Glu Gln Asn Ile Ser Val Arg Arg Arg Gln Gly Val Ser Ile Gly
        130                 135                 140
Arg Leu His Lys Gln Arg Lys Pro Asp Arg Arg Lys Arg Ile Ser Gly
145                 150                 155                 160
Arg
```

(2) INFORMATION FOR SEQ ID NO:9:

(i) SEQUENCE CHARACTERISTICS:
        (A) LENGTH: 149 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:9:

```
Gly Gly Ile Asp Trp Ile Pro Gly Tyr Arg Ala Gln Ile Arg Pro Ile
1               5                   10                  15
Ser Ser Gly Leu Glu Glu Lys Glu Val Val Glu Val Thr Glu Ser Arg
                20                  25                  30
Asp Lys Pro Gly Leu Asn Arg Ser Ser Glu Pro Leu Ser Gly Glu Lys
            35                  40                  45
Tyr Ser Pro Lys Glu Leu Leu Ala Leu Leu Lys Cys Val Glu Ala Glu
    50                  55                  60
Ile Ala Asn Tyr Glu Ala Cys Leu Lys Glu Glu Val Glu Lys Arg Lys
65                  70                  75                  80
Lys Phe Lys Ile Asp Asp Gln Arg Arg Thr His Asn Tyr Asp Glu Phe
                85                  90                  95
Ile Cys Thr Phe Ile Ser Met Leu Ala Gln Glu Gly Met Leu Ala Asn
                100                 105                 110
Leu Val Glu Gln Asn Ile Ser Val Arg Arg Arg Gln Gly Val Ser Ile
            115                 120                 125
Gly Arg Leu His Lys Gln Arg Lys Pro Asp Arg Arg Lys Arg Ser Glu
        130                 135                 140
Arg Pro Ile Asp Arg
145
```

(2) INFORMATION FOR SEQ ID NO:10:

(i) SEQUENCE CHARACTERISTICS:
        (A) LENGTH: 80 base pairs

```
            (B) TYPE: nucleic acid
            (C) STRANDEDNESS: single
            (D) TOPOLOGY: unknown (ii) MOLECULE TYPE: other nucleic acid (xi) SEQUENCE DESCRIPTION: SEQ ID NO:10:

ATGGACCTGT CTGCTCTGCG TGTTGAAGAA GTTCAAAACG TTATCAACGC TATGCAAAAG       60

ATCCTGGAAT GTCCAATCTG                                                  80

(2) INFORMATION FOR SEQ ID NO:11:

(i) SEQUENCE CHARACTERISTICS:
            (A) LENGTH: 101 base pairs
            (B) TYPE: nucleic acid
            (C) STRANDEDNESS: single
            (D) TOPOLOGY: unknown (ii) MOLECULE TYPE: other nucleic acid (xi) SEQUENCE DESCRIPTION: SEQ ID NO:11:

GGTTCAGCAG CTTCAGCATA CAGAACTTAC AGAAGATGTG GTCACACTTA GTGGAAACTG       60

GTTCCTTGAT CAGTTCCAGA CAGATTGGAC ATTCCAGGAT C                         101

(2) INFORMATION FOR SEQ ID NO:12:

(i) SEQUENCE CHARACTERISTICS:
            (A) LENGTH: 102 base pairs
            (B) TYPE: nucleic acid
            (C) STRANDEDNESS: single
            (D) TOPOLOGY: unknown (ii) MOLECULE TYPE: other nucleic acid (xi) SEQUENCE DESCRIPTION: SEQ ID NO:12:

GTATGCTGAA GCTGCTGAAC CAAAAGAAGG GTCCATCTCA ATGTCCACTG TGTAAGAACG       60

ACATCACTAA GCGTTCTCTG CAAGAATCTA CTCGTTTCTC TC                        102

(2) INFORMATION FOR SEQ ID NO:13:

(i) SEQUENCE CHARACTERISTICS:
            (A) LENGTH: 81 base pairs
            (B) TYPE: nucleic acid
            (C) STRANDEDNESS: single
            (D) TOPOLOGY: unknown (ii) MOLECULE TYPE: other nucleic acid (xi) SEQUENCE DESCRIPTION: SEQ ID NO:13:

TTCCAGACCA GTGTCCAGCT GGAAAGCACA GATGATCTTC AGCAGTTCTT CAACCAGTTG       60

AGAGAAACGA GTAGATTCTT G                                                81

(2) INFORMATION FOR SEQ ID NO:14:

(i) SEQUENCE CHARACTERISTICS:
            (A) LENGTH: 31 base pairs
            (B) TYPE: nucleic acid
            (C) STRANDEDNESS: single
            (D) TOPOLOGY: unknown (ii) MOLECULE TYPE: other nucleic acid (xi) SEQUENCE DESCRIPTION: SEQ ID NO:14:

GCTAGAATTC ACCATGGACC TGTCTGCTCT G                                     31
```

(2) INFORMATION FOR SEQ ID NO:15:

(i) SEQUENCE CHARACTERISTICS:
        (A) LENGTH: 28 base pairs
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO:15:

```
GCTAGTCGAC TTCCAGACCA GTGTCCAG                                    28
```

(2) INFORMATION FOR SEQ ID NO:16:

(i) SEQUENCE CHARACTERISTICS:
        (A) LENGTH: 247 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:16:

```
Met Gly Lys Lys Ile Met Thr Asp Ala Gly Ser Trp Cys Leu Ile Glu
  1               5                  10                  15

Ser Asp Pro Gly Val Phe Thr Glu Met Leu Arg Gly Phe Gly Val Asp
             20                  25                  30

Gly Leu Gln Val Glu Glu Leu Tyr Ser Leu Asp Asp Asp Lys Ala Met
         35                  40                  45

Thr Arg Pro Thr Tyr Gly Leu Ile Phe Leu Phe Lys Trp Arg Gln Gly
     50                  55                  60

Asp Glu Thr Thr Gly Ile Pro Ser Asp Lys Gln Asn Ile Phe Phe Ala
 65                  70                  75                  80

His Gln Thr Ile Gln Asn Ala Cys Ala Thr Gln Ala Leu Ile Asn Leu
                 85                  90                  95

Leu Met Asn Val Glu Asp Thr Asp Val Lys Leu Gly Asn Ile Leu Asn
            100                 105                 110

Gln Tyr Lys Glu Phe Ala Ile Asp Leu Asp Pro Asn Thr Arg Gly His
        115                 120                 125

Cys Leu Ser Asn Ser Glu Glu Ile Arg Thr Val His Asn Ser Phe Ser
130                 135                 140

Arg Gln Thr Leu Phe Glu Leu Asp Ile Lys Gly Gly Glu Ser Glu Asp
145                 150                 155                 160

Asn Tyr His Phe Val Thr Tyr Val Pro Ile Gly Asn Lys Val Tyr Glu
                165                 170                 175

Leu Asp Gly Leu Arg Glu Leu Pro Leu Glu Val Ala Glu Phe Gln Lys
            180                 185                 190

Glu Gln Asp Trp Ile Glu Ala Ile Lys Pro Val Ile Gln Gln Arg Met
        195                 200                 205

Gln Lys Tyr Ser Glu Gly Glu Ile Thr Phe Asn Leu Met Ala Leu Val
    210                 215                 220

Pro Asn Arg Lys Gln Lys Leu Gln Glu Met Met Glu Asn Leu Ile Gln
225                 230                 235                 240

Ala Asn Glu Asn Asn Glu Leu
                245
```

(2) INFORMATION FOR SEQ ID NO:17:

(i) SEQUENCE CHARACTERISTICS:

(A) LENGTH: 223 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:17:

Met Gln Leu Lys Pro Met Glu Ile Asn Pro Glu Met Leu Asn Lys Val
1               5                  10                  15

Leu Ser Arg Leu Gly Val Ala Gly Gln Trp Arg Phe Val Asp Val Leu
            20                  25                  30

Gly Leu Glu Glu Glu Ser Leu Gly Ser Val Pro Ala Pro Ala Cys Ala
        35                  40                  45

Leu Leu Leu Phe Pro Leu Thr Ala Gln His Glu Asn Phe Arg Lys
    50                  55                  60

Lys Gln Ile Glu Glu Leu Lys Gly Gln Glu Val Ser Pro Lys Val Tyr
65                  70                  75                  80

Phe Met Lys Gln Thr Ile Gly Asn Ser Cys Gly Thr Ile Gly Leu Ile
                85                  90                  95

His Ala Val Ala Asn Asn Gln Asp Lys Leu Gly Phe Glu Asp Gly Ser
            100                 105                 110

Val Leu Lys Gln Phe Leu Ser Glu Thr Glu Lys Met Ser Pro Glu Asp
        115                 120                 125

Arg Ala Lys Cys Phe Glu Lys Asn Glu Ala Ile Gln Ala Ala His Asp
    130                 135                 140

Ala Val Ala Gln Glu Gly Gln Cys Arg Val Asp Asp Lys Val Asn Phe
145                 150                 155                 160

His Phe Ile Leu Phe Asn Asn Val Asp Gly His Leu Tyr Glu Leu Asp
                165                 170                 175

Gly Arg Met Pro Phe Pro Val Asn His Gly Ala Ser Ser Glu Asp Thr
            180                 185                 190

Leu Leu Lys Asp Ala Ala Lys Val Cys Arg Glu Phe Thr Glu Arg Glu
        195                 200                 205

Gln Gly Glu Val Arg Phe Ser Ala Val Ala Leu Cys Lys Ala Ala
    210                 215                 220

(2) INFORMATION FOR SEQ ID NO:18:

(i) SEQUENCE CHARACTERISTICS:
        (A) LENGTH: 230 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:18:

Met Glu Gly Gln Arg Trp Leu Pro Leu Glu Ala Asn Pro Glu Val Thr
1               5                  10                  15

Asn Gln Phe Leu Lys Gln Leu Gly Leu His Pro Asn Trp Gln Phe Val
            20                  25                  30

Asp Val Tyr Gly Met Asp Pro Glu Leu Leu Ser Met Val Pro Arg Pro
        35                  40                  45

Val Cys Ala Val Leu Leu Leu Phe Pro Ile Thr Glu Lys Tyr Glu Val
    50                  55                  60

Phe Arg Thr Glu Glu Glu Glu Lys Ile Lys Ser Gln Gly Gln Asp Val
65                  70                  75                  80

```
Thr Ser Ser Val Tyr Phe Met Lys Gln Thr Ile Ser Asn Ala Cys Gly
                85                  90                  95

Thr Ile Gly Leu Ile His Ala Ile Ala Asn Asn Lys Asp Lys Met His
            100                 105                 110

Phe Glu Ser Gly Ser Thr Leu Lys Lys Phe Leu Glu Glu Ser Val Ser
            115                 120                 125

Met Ser Pro Glu Glu Arg Ala Arg Tyr Leu Glu Asn Tyr Asp Ala Ile
130                 135                 140

Arg Val Thr His Glu Thr Ser Ala His Glu Gly Gln Thr Glu Ala Pro
145                 150                 155                 160

Ser Ile Asp Glu Lys Val Asp Leu His Phe Ile Ala Leu Val His Val
                165                 170                 175

Asp Gly His Leu Tyr Glu Leu Asp Gly Arg Lys Pro Phe Pro Ile Asn
                180                 185                 190

His Gly Glu Thr Ser Asp Glu Thr Leu Leu Glu Asp Ala Ile Glu Val
                195                 200                 205

Cys Lys Lys Phe Met Glu Arg Asp Pro Asp Glu Leu Arg Phe Asn Ala
                210                 215                 220

Ile Ala Leu Ser Ala Ala
225                 230
```

(2) INFORMATION FOR SEQ ID NO:19:

(i) SEQUENCE CHARACTERISTICS:
        (A) LENGTH: 43 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:19:

```
Leu Leu Arg Cys Ser Arg Cys Thr Asn Ile Leu Arg Glu Pro Val Cys
1               5                   10                  15

Leu Gly Gly Cys Glu His Ile Phe Cys Ser Asn Cys Val Ser Asp Cys
                20                  25                  30

Ile Gly Thr Gly Cys Pro Val Cys Tyr Thr Pro
            35                  40
```

(2) INFORMATION FOR SEQ ID NO:20:

(i) SEQUENCE CHARACTERISTICS:
        (A) LENGTH: 326 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:20:

```
Met Gly Lys Lys Ile Met Thr Asp Ala Gly Ser Trp Cys Leu Ile Glu
1               5                   10                  15

Ser Asp Pro Gly Val Phe Thr Glu Met Leu Arg Gly Phe Gly Val Asp
                20                  25                  30

Gly Leu Gln Val Glu Glu Leu Tyr Ser Leu Asp Asp Lys Ala Met
            35                  40                  45

Thr Arg Pro Thr Tyr Gly Leu Ile Phe Leu Phe Lys Trp Arg Gln Gly
50                  55                  60

Asp Glu Thr Thr Gly Ile Pro Ser Asp Lys Gln Asn Ile Phe Phe Ala
65                  70                  75                  80
```

```
His Gln Thr Ile Gln Asn Ala Cys Ala Thr Gln Ala Leu Ile Asn Leu
                85                  90                  95

Leu Met Asn Val Glu Asp Thr Asp Val Lys Leu Gly Asn Ile Leu Asn
            100                 105                 110

Gln Tyr Lys Glu Phe Ala Ile Asp Leu Asp Pro Asn Thr Arg Gly His
        115                 120                 125

Cys Leu Ser Asn Ser Glu Glu Ile Arg Thr Val His Asn Ser Phe Ser
    130                 135                 140

Arg Gln Thr Leu Phe Glu Leu Asp Ile Lys Gly Gly Glu Ser Glu Asp
145                 150                 155                 160

Asn Tyr His Phe Val Thr Tyr Val Pro Ile Gly Asn Lys Val Tyr Glu
                165                 170                 175

Leu Asp Gly Leu Arg Glu Leu Pro Leu Glu Val Ala Glu Phe Gln Lys
            180                 185                 190

Glu Gln Asp Trp Ile Glu Ala Ile Lys Pro Val Ile Gln Gln Arg Met
        195                 200                 205

Gln Lys Tyr Ser Glu Gly Glu Ile Thr Phe Asn Leu Met Ala Leu Val
    210                 215                 220

Pro Asn Arg Lys Gln Lys Leu Gln Glu Met Met Glu Asn Leu Ile Gln
225                 230                 235                 240

Ala Asn Glu Asn Glu Leu Glu Glu Gln Ile Ala Asp Leu Asn Lys
                245                 250                 255

Ala Ile Ala Asp Glu Asp Tyr Lys Met Glu Met Tyr Arg Lys Glu Asn
            260                 265                 270

Asn Arg Arg His Asn Tyr Thr Pro Phe Val Ile Glu Leu Met Lys
        275                 280                 285

Ile Leu Ala Lys Glu Gly Lys Leu Val Gly Leu Val Asp Asn Ala Tyr
    290                 295                 300

Gln Ala Ala Lys Glu Lys Ser Lys Leu Asn Thr Asp Ile Thr Lys Leu
305                 310                 315                 320

Glu Leu Lys Arg Lys Gln
                325

(2) INFORMATION FOR SEQ ID NO:21:

(i) SEQUENCE CHARACTERISTICS:
        (A) LENGTH: 227 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:21:

Met Leu Thr Trp Thr Pro Leu Glu Ser Asn Pro Glu Val Leu Thr Lys
1               5                   10                  15

Tyr Ile His Lys Leu Ala Val Ser Pro Ala Trp Ser Val Thr Asp Val
            20                  25                  30

Ile Gly Leu Glu Asp Asp Thr Leu Glu Trp Ile Pro Arg Pro Val Lys
        35                  40                  45

Ala Phe Ile Leu Leu Phe Pro Cys Ser Glu Thr Tyr Glu Lys His Arg
    50                  55                  60

Thr Glu Glu His Asp Arg Ile Lys Glu Val Glu Glu Gln His Pro Glu
65                  70                  75                  80

Asp Leu Phe Tyr Met Arg Gln Phe Thr His Asn Ala Cys Gly Thr Val
                85                  90                  95
```

```
Ala Leu Ile His Ser Val Ala Asn Asn Lys Glu Val Asp Ile Asp Arg
            100                 105                 110

Gly Val Leu Lys Asp Phe Leu Glu Lys Thr Ala Ser Leu Ser Pro Glu
        115                 120                 125

Glu Arg Gly Arg Ala Leu Glu Lys Asp Glu Lys Phe Thr Ala Asp His
    130                 135                 140

Glu Ala Leu Ala Gln Glu Gly Gln Thr Asn Ala Ala Asn His Glu Lys
145                 150                 155                 160

Val Ile His His Phe Ile Ala Leu Val Asn Lys Glu Gly Thr Leu Tyr
                165                 170                 175

Glu Leu Asp Gly Arg Lys Ser Phe Pro Ile Lys His Gly Pro Thr Ser
            180                 185                 190

Glu Glu Thr Phe Val Lys Asp Ala Ala Lys Val Cys Lys Glu Phe Met
        195                 200                 205

Ala Arg Asp Pro Asn Glu Val Arg Phe Thr Val Leu Ala Leu Thr Ala
    210                 215                 220

Ala Gln Gln
225

(2) INFORMATION FOR SEQ ID NO:22:

(i) SEQUENCE CHARACTERISTICS:
        (A) LENGTH: 236 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:22:

Met Ser Gly Glu Asn Arg Ala Val Val Pro Ile Glu Ser Asn Pro Glu
1               5                   10                  15

Val Phe Thr Asn Phe Ala His Lys Leu Gly Leu Lys Asn Glu Trp Ala
            20                  25                  30

Tyr Phe Asp Ile Tyr Ser Leu Thr Glu Pro Glu Leu Leu Ala Phe Leu
        35                  40                  45

Pro Arg Pro Val Lys Ala Ile Val Leu Leu Phe Pro Ile Asn Glu Asp
    50                  55                  60

Arg Lys Ser Ser Thr Ser Gln Gln Ile Thr Ser Ser Tyr Asp Val Ile
65                  70                  75                  80

Trp Phe Lys Gln Ser Val Lys Asn Ala Cys Gly Leu Tyr Ala Ile Leu
                85                  90                  95

His Ser Leu Ser Asn Asn Gln Ser Leu Leu Glu Pro Gly Ser Asp Leu
            100                 105                 110

Asp Asn Phe Leu Lys Ser Gln Ser Asp Thr Ser Ser Lys Asn Arg
        115                 120                 125

Phe Asp Asp Val Thr Thr Asp Gln Phe Val Leu Asn Val Ile Lys Glu
    130                 135                 140

Asn Val Gln Thr Phe Ser Thr Gly Gln Ser Glu Ala Pro Glu Ala Thr
145                 150                 155                 160

Ala Asp Thr Asn Leu His Tyr Ile Thr Tyr Val Glu Glu Asn Gly Gly
                165                 170                 175

Ile Phe Glu Leu Asp Gly Arg Asn Leu Ser Gly Pro Leu Tyr Leu Gly
            180                 185                 190

Lys Ser Asp Pro Thr Ala Thr Asp Leu Ile Glu Gln Glu Leu Val Arg
        195                 200                 205
```

```
Val Arg Val Ala Ser Tyr Met Glu Asn Ala Asn Glu Glu Asp Val Leu
    210                 215                 220

Asn Phe Ala Met Leu Gly Leu Gly Pro Asn Trp Glu
225                 230                 235

(2) INFORMATION FOR SEQ ID NO:23:

(i) SEQUENCE CHARACTERISTICS:
        (A) LENGTH: 230 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:23:

Met Glu Gly Gln Arg Trp Leu Pro Leu Glu Ala Asn Pro Glu Val Thr
1               5                   10                  15

Asn Gln Phe Leu Lys Gln Leu Gly Leu His Pro Asn Trp Gln Phe Val
            20                  25                  30

Asp Val Tyr Gly Met Asp Pro Glu Leu Leu Ser Met Val Pro Arg Pro
        35                  40                  45

Val Cys Ala Val Leu Leu Leu Phe Pro Ile Thr Glu Lys Tyr Glu Val
    50                  55                  60

Phe Arg Thr Glu Glu Glu Lys Ile Lys Ser Gln Gly Gln Asp Val
65                  70                  75                  80

Thr Ser Ser Val Tyr Phe Met Lys Gln Thr Ile Ser Asn Ala Cys Gly
                85                  90                  95

Thr Ile Gly Leu Ile His Ala Ile Ala Asn Asn Lys Asp Lys Met His
            100                 105                 110

Phe Glu Ser Gly Ser Thr Leu Lys Lys Phe Leu Glu Glu Ser Val Ser
        115                 120                 125

Met Ser Pro Glu Glu Arg Ala Arg Tyr Leu Glu Asn Tyr Asp Ala Ile
    130                 135                 140

Arg Val Thr His Glu Thr Ser Ala His Glu Gly Gln Thr Glu Ala Pro
145                 150                 155                 160

Ser Ile Asp Glu Lys Val Asp Leu His Phe Ile Ala Leu Val His Val
                165                 170                 175

Asp Gly His Leu Tyr Glu Leu Asp Gly Arg Lys Pro Phe Pro Ile Asn
            180                 185                 190

His Gly Glu Thr Ser Asp Glu Thr Leu Leu Glu Asp Ala Ile Glu Val
        195                 200                 205

Cys Lys Lys Phe Met Glu Arg Asp Pro Asp Glu Leu Arg Phe Asn Ala
    210                 215                 220

Ile Ala Leu Ser Ala Ala
225                 230

(2) INFORMATION FOR SEQ ID NO:24:

(i) SEQUENCE CHARACTERISTICS:
        (A) LENGTH: 223 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:24:

Met Gln Leu Lys Pro Met Glu Ile Asn Pro Glu Met Leu Asn Lys Val
```

```
1               5                   10                  15
Leu Ser Arg Leu Gly Val Ala Gly Gln Trp Arg Phe Val Asp Val Leu
            20                  25                  30
Gly Leu Glu Glu Ser Leu Gly Ser Val Pro Ala Pro Ala Cys Ala
        35                  40                  45
Leu Leu Leu Leu Phe Pro Leu Thr Ala Gln His Glu Asn Phe Arg Lys
50                  55                  60
Lys Gln Ile Glu Glu Leu Lys Gly Gln Glu Val Ser Pro Lys Val Tyr
65                  70                  75                  80
Phe Met Lys Gln Thr Ile Gly Asn Ser Cys Gly Thr Ile Gly Leu Ile
                85                  90                  95
His Ala Val Ala Asn Asn Gln Asp Lys Leu Gly Phe Glu Asp Gly Ser
            100                 105                 110
Val Leu Lys Gln Phe Leu Ser Glu Thr Glu Lys Met Ser Pro Glu Asp
            115                 120                 125
Arg Ala Lys Cys Phe Glu Lys Asn Glu Ala Ile Gln Ala Ala His Asp
        130                 135                 140
Ala Val Ala Gln Glu Gly Gln Cys Arg Val Asp Asp Lys Val Asn Phe
145                 150                 155                 160
His Phe Ile Leu Phe Asn Asn Val Asp Gly His Leu Tyr Glu Leu Asp
                165                 170                 175
Gly Arg Met Pro Phe Pro Val Asn His Gly Ala Ser Ser Glu Asp Thr
            180                 185                 190
Leu Leu Lys Asp Ala Ala Lys Val Cys Arg Glu Phe Thr Glu Arg Glu
            195                 200                 205
Gln Gly Glu Val Arg Phe Ser Ala Val Ala Leu Cys Lys Ala Ala
        210                 215                 220
```

(2) INFORMATION FOR SEQ ID NO:25:

(i) SEQUENCE CHARACTERISTICS:
        (A) LENGTH: 24 base pairs
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO:25:

CCATCTCAAG GTCCACTGTG TAAG                    24

(2) INFORMATION FOR SEQ ID NO:26:

(i) SEQUENCE CHARACTERISTICS:
        (A) LENGTH: 24 base pairs
        (B) TYPE: nucleic acid
        (C) STRANDEDNESS: single
        (D) TOPOLOGY: unknown (ii) MOLECULE TYPE: other nucleic acid (iv) ANTI-SENSE: YES (xi) SEQUENCE DESCRIPTION: SEQ ID NO:26:

CTTACACAGT GGACCTTGAG ATGG                    24

(2) INFORMATION FOR SEQ ID NO:27:

(i) SEQUENCE CHARACTERISTICS:
        (A) LENGTH: 27 base pairs
        (B) TYPE: nucleic acid

```
        (C) STRANDEDNESS: single
        (D) TOPOLOGY: unknown (ii) MOLECULE TYPE: other nucleic acid (xi) SEQUENCE DESCRIPTION: SEQ ID NO:27:

CAATGTCCAC TGGGTAAGAA CGACATC                                            27

(2) INFORMATION FOR SEQ ID NO:28:

(i) SEQUENCE CHARACTERISTICS:
        (A) LENGTH: 27 base pairs
        (B) TYPE: nucleic acid
        (C) STRANDEDNESS: single
        (D) TOPOLOGY: unknown (ii) MOLECULE TYPE: other nucleic acid (iv) ANTI-SENSE: YES (xi) SEQUENCE DESCRIPTION: SEQ ID NO:28:

GATGTCGTTC TTACCCAGTG GACATTG                                            27

(2) INFORMATION FOR SEQ ID NO:29:

(i) SEQUENCE CHARACTERISTICS:
        (A) LENGTH: 79 base pairs
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO:29:

GCATGGATCC TCAAACCTTG TGCAGGCAGG TACCCTGGTC AACAGGAGAC AGGTGGGAAA        60

CCAGGATCTT TTGCATAGC                                                    79

(2) INFORMATION FOR SEQ ID NO:30:

(i) SEQUENCE CHARACTERISTICS:
        (A) LENGTH: 23 base pairs
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO:30:

CCGATGCCCT TGGAATTGAC GAG                                                23

(2) INFORMATION FOR SEQ ID NO:31:

(i) SEQUENCE CHARACTERISTICS:
        (A) LENGTH: 25 base pairs
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO:31:

CGATGAATTC GAGCTAGCTT CTATC                                              25

(2) INFORMATION FOR SEQ ID NO:32:

(i) SEQUENCE CHARACTERISTICS:
        (A) LENGTH: 32 base pairs
        (B) TYPE: nucleic acid
```

```
        (C) STRANDEDNESS: single
        (D) TOPOLOGY: unknown (ii) MOLECULE TYPE: other nucleic acid (xi) SEQUENCE DESCRIPTION: SEQ ID NO:32:

GCATGAATTC TCAGCTCCGG CGCACTGAGA TG                                      32

(2) INFORMATION FOR SEQ ID NO:33:

(i) SEQUENCE CHARACTERISTICS:
        (A) LENGTH: 33 base pairs
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO:33:

GCATGAATTC TCAAGCCAGC ATGGATATGA AGG                                     33

(2) INFORMATION FOR SEQ ID NO:34:

(i) SEQUENCE CHARACTERISTICS:
        (A) LENGTH: 32 base pairs
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO:34:

GCATGAATTC TCAGTCATCA ATCTTGAACT TC                                      32

(2) INFORMATION FOR SEQ ID NO:35:

(i) SEQUENCE CHARACTERISTICS:
        (A) LENGTH: 31 base pairs
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO:35:

GCATGAATTC TCATGCAATC TCGGCTTCTA C                                       31

(2) INFORMATION FOR SEQ ID NO:36:

(i) SEQUENCE CHARACTERISTICS:
        (A) LENGTH: 33 base pairs
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO:36:

GCATGGATCC CCAAGATTGA TGACCAGCGA AGG                                     33

(2) INFORMATION FOR SEQ ID NO:37:

(i) SEQUENCE CHARACTERISTICS:
        (A) LENGTH: 22 base pairs
        (B) TYPE: nucleic acid
        (C) STRANDEDNESS: single
        (D) TOPOLOGY: unknown (ii) MOLECULE TYPE: other nucleic acid
```

(xi) SEQUENCE DESCRIPTION: SEQ ID NO:37:

GCTGGCCAAC CCGGTGGAAC AG                                    22

(2) INFORMATION FOR SEQ ID NO:38:

(i) SEQUENCE CHARACTERISTICS:
        (A) LENGTH: 22 base pairs
        (B) TYPE: nucleic acid
        (C) STRANDEDNESS: single
        (D) TOPOLOGY: unknown (ii) MOLECULE TYPE: other nucleic acid (iv) ANTI-SENSE: YES (xi) SEQUENCE DESCRIPTION: SEQ ID NO:38:

CTGTTCCACC GGGTTGGCCA GC                                    22

(2) INFORMATION FOR SEQ ID NO:39:

(i) SEQUENCE CHARACTERISTICS:
        (A) LENGTH: 56 base pairs
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO:39:

CCTGTTATTA ACCCTCACTA AAGGGAAGGG TACCATGAAT AAGGGCTGGC TGGAGC     56

(2) INFORMATION FOR SEQ ID NO:40:

(i) SEQUENCE CHARACTERISTICS:
        (A) LENGTH: 20 base pairs
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO:40:

GAAGCGGATG TCGTGGTAGG                                       20

(2) INFORMATION FOR SEQ ID NO:41:

(i) SEQUENCE CHARACTERISTICS:
        (A) LENGTH: 22 base pairs
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO:41:

GATGTATATA ACTATCTATT CG                                    22

(2) INFORMATION FOR SEQ ID NO:42:

(i) SEQUENCE CHARACTERISTICS:
        (A) LENGTH: 34 base pairs
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO:42:

GCATAGATCT TCACCCCTGG CTGCCTTGGA TTGG 34

(2) INFORMATION FOR SEQ ID NO:43:

(i) SEQUENCE CHARACTERISTICS:
        (A) LENGTH: 20 base pairs
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO:43:

GAAGCGGATG TCGTGGTAGG 20

(2) INFORMATION FOR SEQ ID NO:44:

(i) SEQUENCE CHARACTERISTICS:
        (A) LENGTH: 22 base pairs
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO:44:

GATGTATATA ACTATCTATT CG 22

(2) INFORMATION FOR SEQ ID NO:45:

(i) SEQUENCE CHARACTERISTICS:
        (A) LENGTH: 29 base pairs
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO:45:

CGTAGTCGAC TGTCAGCGCC AGGGGACTC 29

(2) INFORMATION FOR SEQ ID NO:46:

(i) SEQUENCE CHARACTERISTICS:
        (A) LENGTH: 19 base pairs
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO:46:

CAACCCCACT CCCATTGTC 19

(2) INFORMATION FOR SEQ ID NO:47:

(i) SEQUENCE CHARACTERISTICS:
        (A) LENGTH: 20 base pairs
        (B) TYPE: nucleic acid
        (C) STRANDEDNESS: single
        (D) TOPOLOGY: unknown -continued

```
    (ii) MOLECULE TYPE: other nucleic acid (iv) ANTI-SENSE: YES (xi) SEQUENCE DESCRIPTION: SEQ ID NO:47:

GAGTTGGTGT TCTGCACGTC                                                  20
```